United States Patent
Cioanta et al.

(10) Patent No.: US 6,682,555 B2
(45) Date of Patent: Jan. 27, 2004

(54) METHODS FOR TREATING THE PROSTATE AND INHIBITING OBSTRUCTION OF THE PROSTATIC URETHRA USING BIODEGRADABLE STENTS

(75) Inventors: Iulian Cioanta, Cary, NC (US); Richard Barry Klein, Cary, NC (US)

(73) Assignee: WIT IP Corporation, Southborough, MA (US)

( * ) Notice: Subject to any disclaimer, the term of this patent is extended or adjusted under 35 U.S.C. 154(b) by 108 days.

(21) Appl. No.: 10/011,494

(22) Filed: Nov. 13, 2001

(65) Prior Publication Data

US 2002/0082610 A1 Jun. 27, 2002

Related U.S. Application Data

(60) Provisional application No. 60/248,109, filed on Nov. 13, 2000.

(51) Int. Cl.[7] .................................................. A61F 2/06
(52) U.S. Cl. ............................. 623/1.21; 604/101.03; 604/103.1
(58) Field of Search ........................ 623/1.11, 1.21, 623/23.7, 23.66; 606/194; 604/101.1, 101.2, 101.05, 103.01, 103.02

(56) References Cited

U.S. PATENT DOCUMENTS

| | | | |
|---|---|---|---|
| 2,024,301 A | 12/1935 | Norwood | 128/255 |
| 2,074,634 A | 3/1937 | Ackermann | 128/401 |
| 2,076,638 A | 4/1937 | Haynos | 128/401 |
| 2,077,453 A | 4/1937 | Albright | 128/254 |
| 2,078,786 A | 4/1937 | Wood | 128/401 |
| 2,168,427 A | 8/1939 | McConkey | 128/344 |
| 2,190,383 A | 2/1940 | Newman | 128/401 |
| 2,190,384 A | 2/1940 | Newman | 128/400 |
| 3,045,677 A | 7/1962 | Wallace | 128/349 |
| 3,811,450 A | 5/1974 | Lord | 128/349 R |
| 4,435,590 A | 3/1984 | Shalaby et al. | 560/61 |
| 4,441,496 A | 4/1984 | Shalaby et al. | 128/335.5 |
| 4,532,928 A | 8/1985 | Bezwada et al. | 128/335.5 |
| 4,559,945 A | 12/1985 | Koelmel et al. | 128/335.5 |

(List continued on next page.)

FOREIGN PATENT DOCUMENTS

| | | | |
|---|---|---|---|
| EP | 0449472 A1 | 3/1991 | A61F/7/12 |
| WO | WO97/02794 | 1/1997 | A61F/7/12 |

OTHER PUBLICATIONS

Buzelin et al., *Comparison of tamsulosin with alfuzosin in the treatment of patients with lower urinary tract symptoms suggestive of bladder outlet obstruction (symptomatic benign prostatic hyperplasia)*, Br J Urol, 80:597–605 (1997).

Cabelin et al., *Benign prostatic hyperplasia: challenges for the new millennium*, Curr Opin Urol Jul, 10(4):301–306 (2000).

Caine et al. *Adrenergic and cholinergic receptors in the human prostate, prostatic capsule and bladder neck*, Br J. Urol, 47:193–202 (1975).

(List continued on next page.)

*Primary Examiner*—Bruce E Snow
(74) *Attorney, Agent, or Firm*—Ganz Law, PC; Bradley M. Ganz; James L. Wolfe

(57) ABSTRACT

Methods of treating the prostate include administering a thermal ablation therapy and inhibiting the obstruction or closure of the prostatic urethral opening by forming a biodegradable stent in situ in the subject such that the stent attaches to the walls of the prostatic urethra. A related method of treating BPH includes thermally treating or ablating localized tissue in the prostate with a treatment catheter and inserting flowable stent material via the treatment catheter into the prostate (either before, during, or after the thermal treatment), forming the flowable stent material so that it defines a stent that remains in position after removal of the treatment catheter to inhibit the closure of the urinary passage. Associated stents and catheters are included.

2 Claims, 18 Drawing Sheets

U.S. PATENT DOCUMENTS

| | | | |
|---|---|---|---|
| 4,605,730 A | 8/1986 | Shalaby et al. | 128/357 |
| 4,649,921 A | 3/1987 | Koelmel et al. | 128/335.5 |
| 4,700,704 A | 10/1987 | Jamiolkowski et al. | 128/335.5 |
| 4,702,917 A | 10/1987 | Schindler | 424/422 |
| 4,743,257 A | 5/1988 | Törmälä et al. | 623/16 |
| 5,087,244 A | 2/1992 | Wolinsky et al. | 604/53 |
| 5,102,402 A | 4/1992 | Dror et al. | 604/265 |
| 5,257,977 A | 11/1993 | Eshel | 604/113 |
| 5,509,929 A | 4/1996 | Hascoet et al. | 607/101 |
| 5,514,178 A | 5/1996 | Torchio | 623/12 |
| 5,549,559 A | 8/1996 | Eshel | 604/113 |
| 5,575,815 A | 11/1996 | Slepian et al. | 623/1 |
| 5,588,965 A * | 12/1996 | Burton et al. | 604/101 |
| 5,599,307 A * | 2/1997 | Bacher et al. | 604/101 |
| 5,634,946 A | 6/1997 | Slepian | 623/11 |
| 5,662,609 A | 9/1997 | Slepian | 604/101 |
| 5,665,063 A * | 9/1997 | Roth et al. | 604/53 |
| 5,674,192 A | 10/1997 | Sahatjian et al. | 604/28 |
| 5,674,287 A | 10/1997 | Slepian et al. | 623/11 |
| 5,766,209 A | 6/1998 | Devonec | 604/8 |
| 5,876,417 A | 3/1999 | Devonec et al. | 606/192 |
| 5,899,917 A | 5/1999 | Edwards et al. | 606/195 |
| 6,171,338 B1 | 1/2001 | Talja et al. | 623/11.11 |
| 6,299,597 B1 * | 10/2001 | Buscemi et al. | 604/101.03 |
| 6,338,726 B1 * | 1/2002 | Edwards et al. | 604/101.03 |

OTHER PUBLICATIONS

Caine et al., *Dynamics of acute retention in prostatic patient and role of adrenergic receptors*, Urology, 9:399–403 (1977).

Carruthers, SG, *Adverse effects of alpha$\alpha_1$–adrenergic blocking drugs*, Drug Safety, 11:12–20 (1994).

Chapple et al., *Alpha$_1$–adrenoceptor subtypes in the human prostate*, Br J Urol, 74:585–589 (1994).

Chapple et al., *Characterisation of human prostatic adrenoceptors using pharmacology receptor binding and localization*, Br J Urol, 63:487–496 (1989).

Chapple, CR, *Pharmacotherapy for benign prostatic hyperplasia—the potential for alpha$\alpha_1$ adrenoceptor subtype-specific blockade*, Br J Urol, 81:23–37 (1998).

Danilychev et al., *Improving Adhesion Characteristics of Wire Insulation Surfaces*, Wire Technology International, pp. 93–97 (Mar. 1994).

Furuya et al., *Alphaadrenergic activity and urethral pressure in prostatic zone in benign prostatic hypertrophy*, J Urol, 128:836–839 (1982).

Guenette et al., *The role of growth factors in the suppression of active cell death in the prostate: An hypothesis*, Biochem Cell Biol, 72:553–559 (1994).

Hieble et al., *International Union of Pharmocology. X. Recommendation of nomenclature of alpha$\alpha_1$–adrenoceptors: consensus update*, Pharmacol Rev, 47:267–270 (1995).

Kaplan et al., *Tolerabiltyt of alpha$_1$–blockade with doxazosin as a therapeutic option for symptomatic benign prostatic hyperplasia in the elderly patient: a pooled analysis of seven double–blind, placebo–controlled studies*, J Gerontol A Biol Sci, 53:M201–M206 (1998).

Kobayashi et al., *Characterisation and localization of prostatic alpha1 adrenoceptors using radioligand receptor binding on slide mounted tissue section*, J Urol, 150:2002–2006 (1993).

Kyprianou et al., *Apoptotic versus proliferative activities in human benigh prostatic hyperplasia*, Hum Pathol, 27:668–675 (1996).

Kyprianou et al., *Induction of prostate apoptosis by doxazosin in benign prostatic hyperplasia*, J Urol, 159:1810–1815 (1998).

Lam et al., *Use of Prostatic Stents for the Treatment of Benign Prostatic Hyperplasia in High–risk Patients*, Benign Prostatic Hyperplasia, pp. 277–284 (2001).

Lowe, FC, *Safety assessment of terazosin in the treatment of patients with symptomatic benign prostatic hyperplasia: a combined analysis*, Urology, 44:46–51 (1994).

McNeill et al., *Sustained–release alfuzosin and trial without catheter after acute urinary retention: a prospective, placebo–controlled trial*, Br J Urol Int, 84:622–627 (1999).

Muramatsu et al., *Pharmacological characterization of alpha$_1$–adrenoceptor subtypes in the human prostate: functional and binding studies*, Br J Urol, 74:572–577 (1994).

Nasu et al., *Quantification and distribution of alpha 1–adrenoceptor subtype mRNAs in human prostate: comparison of benign hypertrophied tissue and nonhypertrophied tissue*, Br J Pharmacol, 119:797–803 (1996).

Perlberg et al., *Adrenergic response to bladder muscle in prostatic obstruction*, Urology, 20:524–527 (1982).

Reuther et al., *Acute retention of urine due to benign prostatic obstruction treated with alpha–adrenergic blockers*, Urol Int, 39:114–115 (1984).

Sahagian, R., *Critical insight: Marking devices with radiopaque coatings*, Medical Device & Diagnostic Industry (May, 1999).

Yamada et al., *Alpha$_1$–adrenoceptors in human prostate: characterization and binding characteristics of alpha$_1$–antagonists*, Life Sci, 54:1845–1854 (1994).

PCT International Search Report, International Application No. PCT/US01/47789 dated Nov. 13, 2001.

* cited by examiner

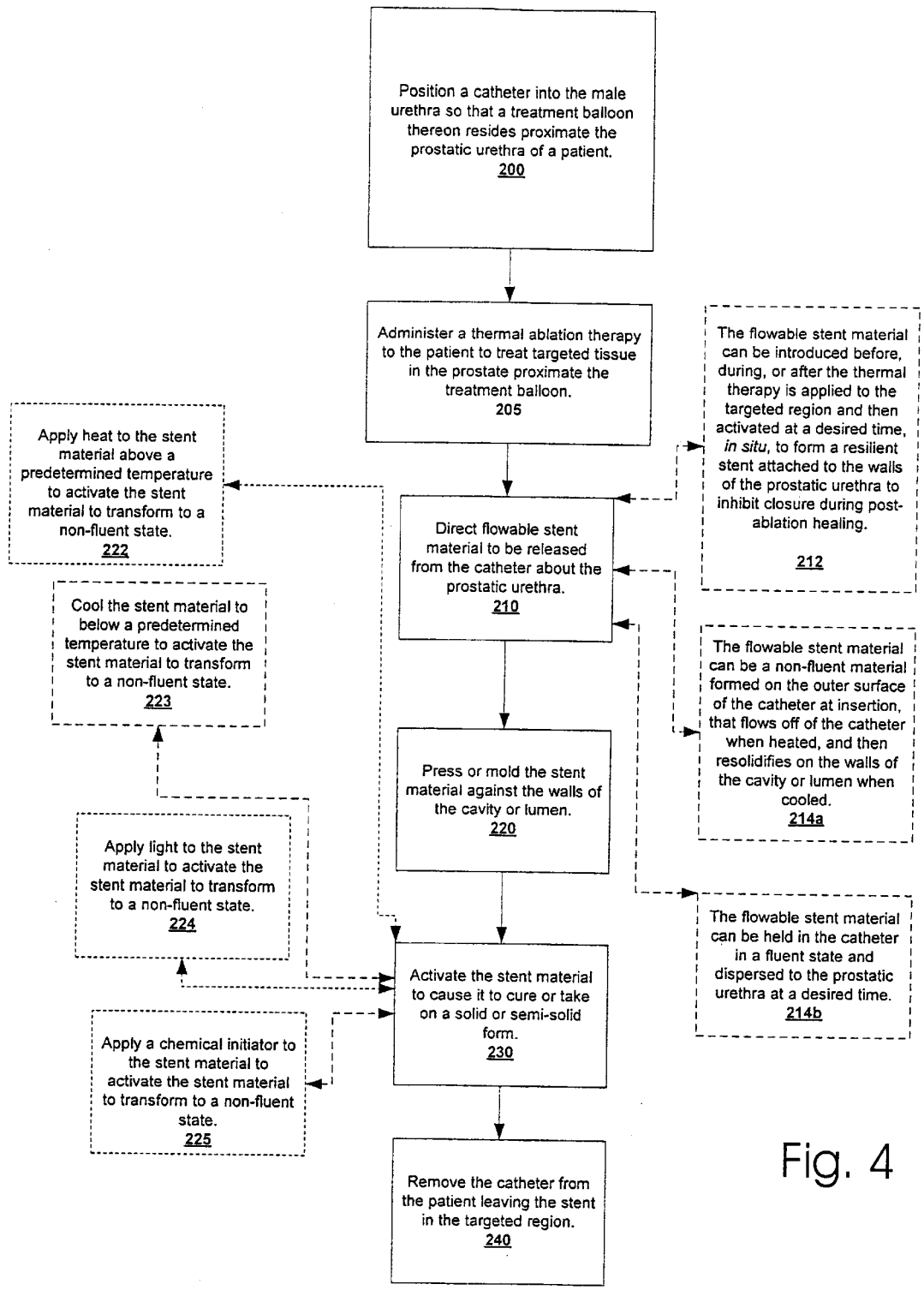

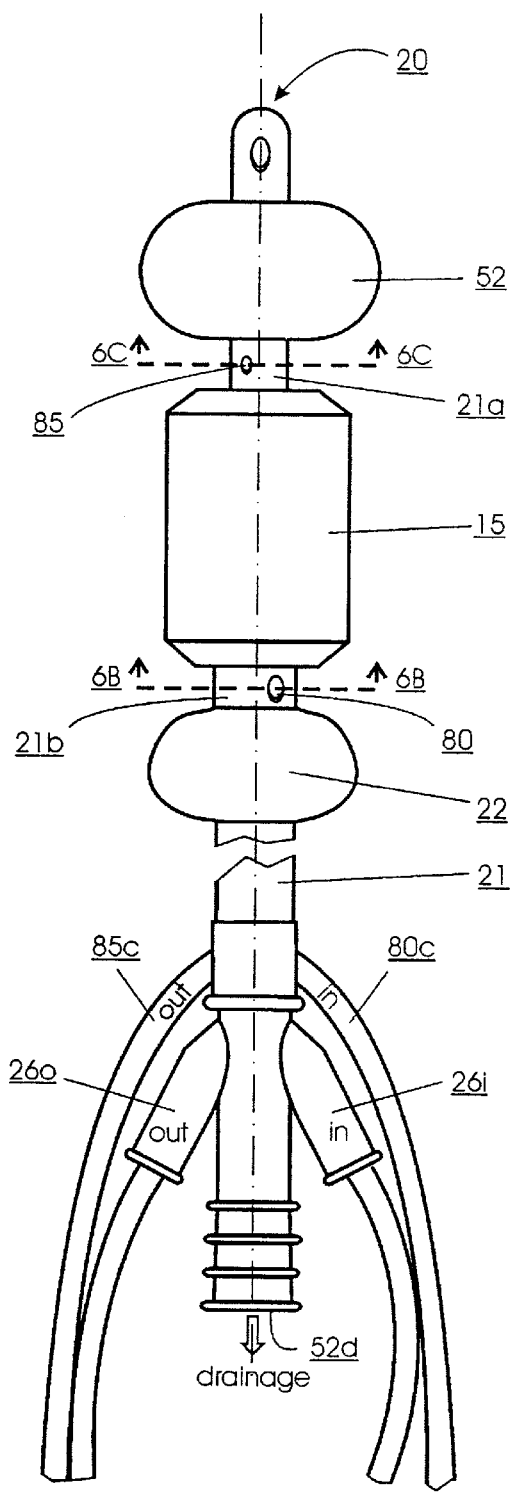
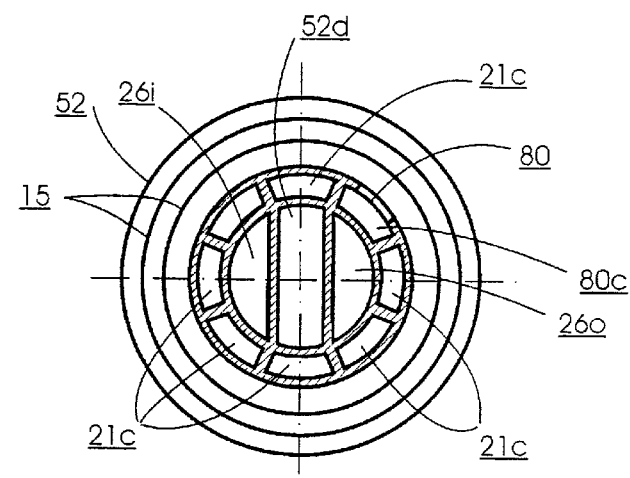
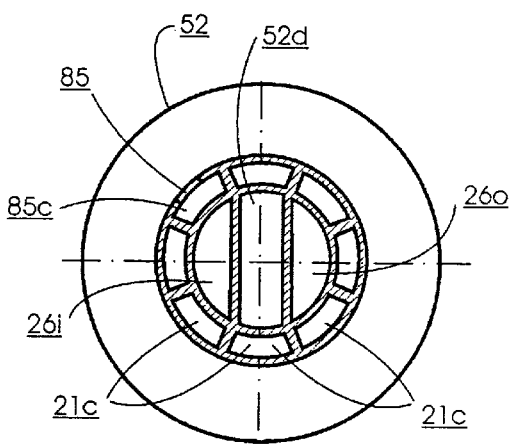
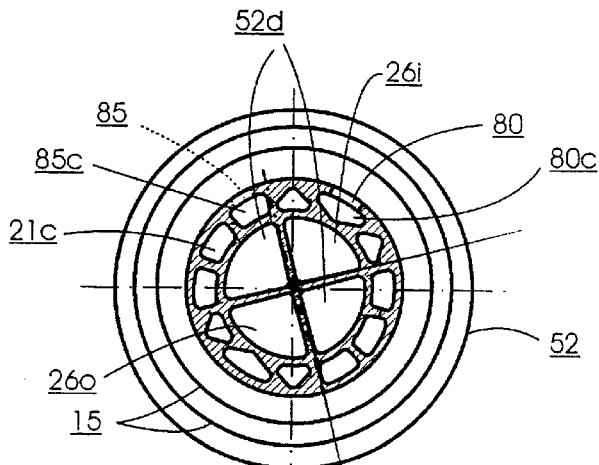
Fig. 6A
Fig. 6B
Fig. 6C
Fig. 6D

METHODS FOR TREATING THE PROSTATE AND INHIBITING OBSTRUCTION OF THE PROSTATIC URETHRA USING BIODEGRADABLE STENTS

RELATED APPLICATIONS

This application claims the benefit of priority from U.S. Provisional Application Serial No. 60/248,109 filed Nov. 13, 2000, the contents of which are hereby incorporated by reference as if recited in full herein.

FIELD OF THE INVENTION

The present invention relates to methods for treating the prostate and/or prostatic urethral stents configured for use after thermal ablation treatments.

BACKGROUND OF THE INVENTION

Conventionally, several types of thermal treatment systems have been proposed to treat certain pathologic conditions of the body by heating or thermally ablating targeted tissue. These thermal treatment systems have used various heating sources to generate the heat necessary to treat or ablate the targeted tissue. For example, laser, microwave, ultrasound, and radio-frequency (RF) energy sources have been proposed to produce the heat that is then directed to the targeted tissue in or around the selected body cavity. These types of thermal treatment systems have been used to thermally ablate the prostate (as well as other organs, body cavities, and/or natural lumens).

One particularly successful thermal ablation system thermally ablates the prostate by a thermocoagulation process. This thermal ablation system employs a closed loop liquid or water-induced thermotherapy (WIT) system which heats liquid, typically water, external to the body and then directs the circulating heated water into a treatment catheter which is inserted through the penile meatus and held in position in the subject undergoing treatment to expose localized tissue to ablation temperatures. The treatment catheter includes an upper end portion which, in operation, is anchored against the bladder neck and an inflatable treatment segment which is held relative to the anchored upper end portion such that it resides along the desired treatment region of the prostate. In operation, the treatment segment expands, in response to the captured circulating fluid traveling therethrough, to press against the localized or targeted tissue in the prostate to expose the tissue to increased temperatures associated with the circulating liquid, thereby thermally ablating the tissue at the treatment site. In addition, the pressurized contact can reduce the heat sink effect attributed to blood circulation in the body, thus enhancing the depth penetration of the heat introduced by the inflatable treatment segment into the prostatic tissue.

As an acceptable alternative to surgery (transurethral resection of the prostate (TURP)), the use of WIT has been shown to be particularly suitable for the treatment of BPH (benign prostatic hyperplasia). Generally stated, the term "BPH" refers to a condition wherein the prostate gland enlarges and the prostatic tissue increases in density which can, unfortunately, tend to close off the urinary drainage path. This condition typically occurs in men as they age due to the physiological changes of the prostatic tissue (and bladder muscles) over time. To enlarge the opening in the prostatic urethra (without requiring surgical incision and removal of tissue), the circulating hot water is directed through the treatment catheter, which is inserted into the penile meatus up through the penile urethra and into the prostate as described above. The treatment segment expands with the hot water held therein to press the inflated treatment segment against the prostate, which then conductively heats and thermally ablates the prostatic tissue. The circulating water is typically heated to a temperature of about 60–62° C. and the targeted tissue is thermally treated for a period of about 45 minutes to locally kill the tissue proximate the urinary drainage passage in the prostate and thereby enlarge the urinary passage through the prostate.

Subsequent to the delivery of the thermal ablation treatment, the treated tissue in the prostate undergoes a healing process. Initially, the ablated tissue can expand or swell due to inflammation or edema which can undesirably block or obstruct the prostatic urethra. Further, during the healing period, portions of the treated tissue can slough off and create an undesirable and unduly limited opening size. Thus, to facilitate proper healing and to enhance the efficacy of the ablation therapy, either the treatment catheter is left in the subject for a period of time and/or the treatment catheter is removed and a post-treatment catheter, such as a conventional Foley catheter, is reinserted and positioned in the subject. However, removal of the treatment catheter and reinsertion of another catheter or stent may cause the tissue along the insertion path and/or treatment region to experience additional irritation. In addition, the amount of time that the treatment or post-treatment catheter must reside in the subject can be from 2–14 days, or even longer. Therefore, it is desirable to configure the post-treatment stent in a minimally invasive manner to allow normal operation of the sphincter, remove the need for the use of an incontinence bag, and reduce the inconvenience or discomfort to the user.

Conventionally, Foley-type catheters with bladder anchoring balloons located on an upper end portion have been used as post-treatment catheters to allow the thermally ablated tissue to mold around the catheter perimeter during the initial healing phase. While these type catheters allow the post-treatment catheter to be securely positioned relative to the bladder neck of the subject, natural operation of the sphincter is inhibited, and the configuration is relatively cumbersome (in position it extends through the penile urethra) and can be considered unduly invasive by the user and may increase the risk of urinary tract infection (UTI) when in position in the subject (particularly, when used for extended periods of time). Other post-treatment catheter configurations (also known as "indwelling catheters" and "stents") have also been proposed; however, some of the catheter types can inhibit the ability to flush out blood clots which may exist from the therapy, and others are undesirably invasive to the user and/or prevent or inhibit the natural operation of the sphincter. Still others are not able to be properly located within the prostatic cavity about the treatment region and/or are unable to retain their desired position in the prostate over time. Still others can, during prolonged use, promote muscle atrophy and/or localized tissue necrosis.

Examples of known post-treatment catheters or stents are described in U.S. Pat. No. 5,916,195 to Eshel et al., U.S. Pat. Nos. 5,876,417 and 5,766,209 to Devonec et al., and U.S. Pat. No. 3,811,450 to Lord. However, there remains a need to provide improved and/or minimally invasive stents and/or post-treatment catheters or stents that are cost effective and can be positioned in the body, such as in the prostate, proximate the treated tissue, to inhibit the restriction of the cavity or natural lumen. There remains a particular need to provide a prostatic stent that is suitable for use during a post thermal therapeutic treatment (such as ablation) healing process or cycle that can inhibit the closure of the urethra in a manner that reduces abrasion, trauma, or irritation that may be introduced to sensitive tissue along the urethra over conventional treatment procedures.

OBJECTS AND SUMMARY OF THE INVENTION

It is therefore an object of the present invention to provide a biodegradable and/or biocompatible prostatic stent that that can be formed in situ via use of the treatment catheter and is suitable for inhibiting post thermal ablation therapy obstruction in the prostate.

It is another object of the present invention to provide methods to inhibit obstruction in an intermittent or periodic flow passage of natural cavities or lumens in the body to keep the flow passage sufficiently open such that the subject is able to discharge or intake fluids in a substantially normal manner.

It is another object of the present invention to deliver flowable stent material into the patient via the treatment catheter and then to form the stent to conform and be in intimate contact with the walls of the prostatic urethra in situ so as to inhibit obstruction in a lumen or cavity during a healing cycle.

These and other objects are satisfied by the present invention that provides, inter alia, methods for treating the prostate and concurrently forming biocompatible and/or biodegradable stents in the urethra during the same treatment session. In particular embodiments, the stent can be delivered and formed in the prostatic urethra so that it resides above the sphincter, and below the bladder neck, and more particularly, substantially between the bladder neck and the verumontanum. Similarly, the present invention includes methods of treating BPH (and other prostate conditions) in a manner that inhibits obstruction in the prostatic urethra during a healing period after a thermal ablation treatment therapy.

Certain embodiments of the present invention are directed to methods of treating a condition of the prostate and forming a prostatic stent in situ in the prostatic urethra. The method includes: (a) introducing a catheter having an expandable treatment balloon thereon into the male urethra of the subject so that the treatment balloon resides proximate the prostatic urethra; (b) administering a thermal ablation therapy to the prostatic urethra of the subject via the treatment catheter, wherein the thermal ablation therapy has a duration of at least about 10 minutes; (c) releasing biocompatible biodegradeable fluent stent material from the catheter; (d) pressing the fluent stent material into intimate contact with the interior surface of the prostatic urethra by using the expandable treatment balloon; (e) activating the biocompatible stent material in situ to cause it to attach and conform to the interior surface of the prostatic urethra so as to take on a non-fluent form to define a stent having sufficient strength and/or thickness to inhibit closure of the prostatic urethra after administration of the thermal therapy; and (f) then removing the treatment catheter leaving the stent in position in the prostatic urethra.

In other embodiments, the pressing step is optional.

Other embodiments are directed to methods of treating BPH. The methods include: (a) thermally ablating localized tissue in the prostate with a treatment catheter having an expandable treatment balloon thereon; (b) flowing fluent viscous or semi-viscous biocompatible and biodegradeable stent material from the treatment catheter into the prostate; (c) molding the flowable stent material to contact the interior surface of the prostatic urethra by expanding the treatment balloon to press the stent material away from the treatment balloon toward the interior surface of the prostatic urethra; (d) securing the stent material to the prostatic urethra so that it defines a resilient conformable stent that remains in position after removal of the treatment catheter to inhibit the closure of the urinary passage; and (e) removing the treatment catheter from the body of the subject.

Other embodiments of the present invention are directed to catheters for treating a condition of the prostate. The catheter includes: (a) an elongated axially extending shaft; (b) a treatment balloon secured to the shaft and configured to expand outwardly therefrom, the treatment balloon configured to apply a thermal therapy to targeted tissue in the body; (c) a bladder anchoring balloon secured to the shaft above the treatment balloon and configured to expand outwardly from the shaft (that can, in certain embodiments, also substantially securely contact the tissue to define a seal about the upper region above the treatment balloon); (d) a sealing balloon secured to the shaft below the treatment balloon and configured to expand outwardly from the shaft; (e) a urinary drainage channel extending through the shaft; and (f) a flowable biocompatible and biodegradable stent material channel having at least one ejection port formed in the shaft associated therewith, the flowable material channel being in fluid isolation with the drainage channel. The shaft is configured and sized such that the portion intermediate the treatment balloon and anchoring balloon has a decreased cross-sectional width relative to the portion of the shaft intermediate the treatment balloon and sealing balloon thereby allowing easy extraction of the catheter after the stent is formed. In operation, the sealing balloon and the bladder-anchoring balloon are in an expanded configuration when flowable biodegradable stent material is directed to exit the ejection port.

In particular embodiments, the catheter can include at least one flushing port and associated flushing channel disposed in the shaft above the at least one dispersing and/or ejection port. In operation, the flushing port is configured to receive flowable stent material therein and direct it to flow out of the body of the subject in the flushing channel to thereby allow a clinician to verify that the flowable stent material has traveled about the prostatic urethra. A sufficient quantity of flowable stent material can be introduced so as to substantially fill the cavity between the treatment balloon and the walls of the prostatic urethra. In addition, the flushing port may be configured to have a reduced size relative to the ejection/dispersing port to facilitate proper filling of the cavity.

Other embodiments include catheters for treating a condition of the prostate that include (a) an elongated axially extending shaft; (b) a treatment balloon secured to the shaft and configured to expand outwardly therefrom; (c) a bladder anchoring balloon secured to the shaft above the treatment balloon and configured to expand outwardly from the shaft; (d) a urinary drainage channel extending through the shaft; and (f) a non-fluent transformable biodegradeable and biocompatible stent material layer formed over the outer surface of the treatment balloon, whereby when exposed to predetermined temperatures, the stent material is configured to become fluent and released from the treatment balloon to flow to surrounding regions in the prostatic urethra and then, upon exposure to different predetermined temperatures, is configured to become non-fluent and remain in intimate contact with the interior surface of the prostatic urethra to define biocompatible biodegradable stent.

In particular embodiments, the shaft is configured and sized such that the portion intermediate the treatment balloon and anchoring balloon has a decreased cross-sectional width relative to the portion of the shaft immediately below the treatment balloon to allow for ease of extraction of the catheter after the stent is formed in situ.

Other catheters include: (a) an elongated axially extending shaft; (b) a treatment balloon secured to the shaft and configured to expand outwardly therefrom; (c) an outwardly expandable permeable or porous sleeve configured to overlie the treatment balloon, the sleeve being independently inflatable from the treatment balloon; (d) a quantity of flowable biocompatible biodegradable stent material disposed intermediate the treatment balloon and the sleeve; (e) a bladder anchoring balloon secured to the shaft above the treatment balloon and configured to expand outwardly from the shaft; (f) a sealing balloon secured to the shaft below the treatment balloon and configured to expand outwardly from the shaft; (f) a urinary drainage channel extending through the shaft; and (g) a flowable fluent biocompatible stent material channel having at least one ejection port formed in the shaft in fluid communication with the sleeve so as to direct the flowable biocompatible stent material therein, the flowable material channel being in fluid isolation with the drainage channel. In operation, the treatment balloon is adapted to inflate to press the flowable stent material released from the sleeve into the targeted tissue in the body.

Still other embodiments are directed to biodegradable stents for the prostatic urethra. The stent is defined by a non-fluent biodegradable biocompatible polymeric material that is in intimate contact with tissue on the surface of the prostatic urethra and extends a distance into a plurality of the acini (prostate ducts), the biodegradable stent having sufficient thickness and length to inhibit closure of the urinary flow passage through the prostatic urethra. The stent may be employed post-treatment (to attach to ablated tissue) or for hyperplasia or other prostate or urinary tract conditions.

Another aspect of the present invention is a set of prostatic treatment catheters, each configured for insertion into the male urethra of a subject as stated above. However, the set is provided such that each is sized a different length to allow customized fit to a particular subject (the portion of the stent body which is adapted to reside in the prostatic urethra itself).

Advantageously, the present invention provides catheters, methods, and/or post-treatment biocompatible stents that can be delivered via the treatment catheter (before, during, or after active administration of the treatment) in a treatment session so as to inhibit prostate obstruction in the urinary drainage path during post-treatment healing. The stents can be made to be biodegradable (that includes bioabsorbable and the like) and configured to reside in the subject above the sphincter during the healing cycle. As the ablated tissue is sloughed off the surface, the stent will be absorbed or discharged from the body. In certain embodiments, the stent will be gradually absorbed and/or flushed out of the subject over about 3 weeks–6 months. In operation, the stent can be configured so as to have sufficient thickness and resilience to allow drainage and/or flushing liquids to be directed into the subject therethrough even for a patient undergoing increased internal pressures due to edema during a healing period after a thermal ablation therapy has been applied to a localized region of the prostate. The instant invention can also reduce irritation introduced to the ablated tissue (which can reduce the number of blood clots produced by the subject) over conventional procedures by eliminating the requirement of inserting a physical conventional mechanical type stent.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4 is a block diagram of operations suitable for carrying out embodiments of the present invention.

FIG. 6A is a front view of another treatment catheter according to other embodiments of the present invention configured to provide the biocompatible biodegradable stent.

FIG. 6B is a sectional view of a treatment catheter taken along lines 6B—6B of FIG. 6A according to embodiments of the present invention.

FIG. 6C is a sectional view of a treatment catheter taken along lines 6C—6C of FIG. 6A according to embodiments of the present invention.

FIG. 6D is an alternate configuration of the sectional view shown in FIG. 6B according to embodiments of the present invention.

DETAILED DESCRIPTION OF EMBODIMENTS OF THE INVENTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the figures, certain elements or features may be exaggerated for clarity and broken lines indicate optional features and/or operations. Like numbers refer to like elements throughout.

The term "thermal ablation" refers to exposing the targeted tissue to a temperature that is sufficient to kill the tissue. In certain embodiments, the thermal ablation is carried out by exposing the targeted tissue to thermocoagulation via a catheter inserted into the subject which is configured to direct circulating hot liquid that is held captured in the catheter and treatment balloon, and which is heated external of the body of the subject, to the targeted treatment region. In any event, in operation, the targeted tissue is exposed to an elevated temperature that is greater than or equal to about 45° C. for a predetermined period of time. In other embodiments, other treatment types can also be used such as surgical resection or other thermal therapies, particularly those that can generate inflammation in the body. The catheters or methods employing biodegradable biocompatible stents according to the present invention may also be appropriate for use in other treated natural lumens or body cavities having intermittent or periodic flow (into, out of, or through) such as the colon, the uterus, the cervix, the throat, the respiratory passages, the ear, the nose, and the like, to inhibit closure or restriction thereof.

In certain embodiments, the thermal ablation is directed to treating conditions of the prostate such as cancer and/or BPH. In so doing, the prostatic tissue can be exposed to a temperature that is at or above 50° C.–62° C. for a treatment period that is typically about 10–60 minutes or longer, and typically between about 20–60 minutes in duration. In certain embodiments, the treatment temperature can be at about 60° C.–62° C. In other embodiments, temperatures of 45° C.–50° C. may be used. Combinations of different ablation level temperatures with different associated and/or cumulative durations may also be employed.

Figure 1A:
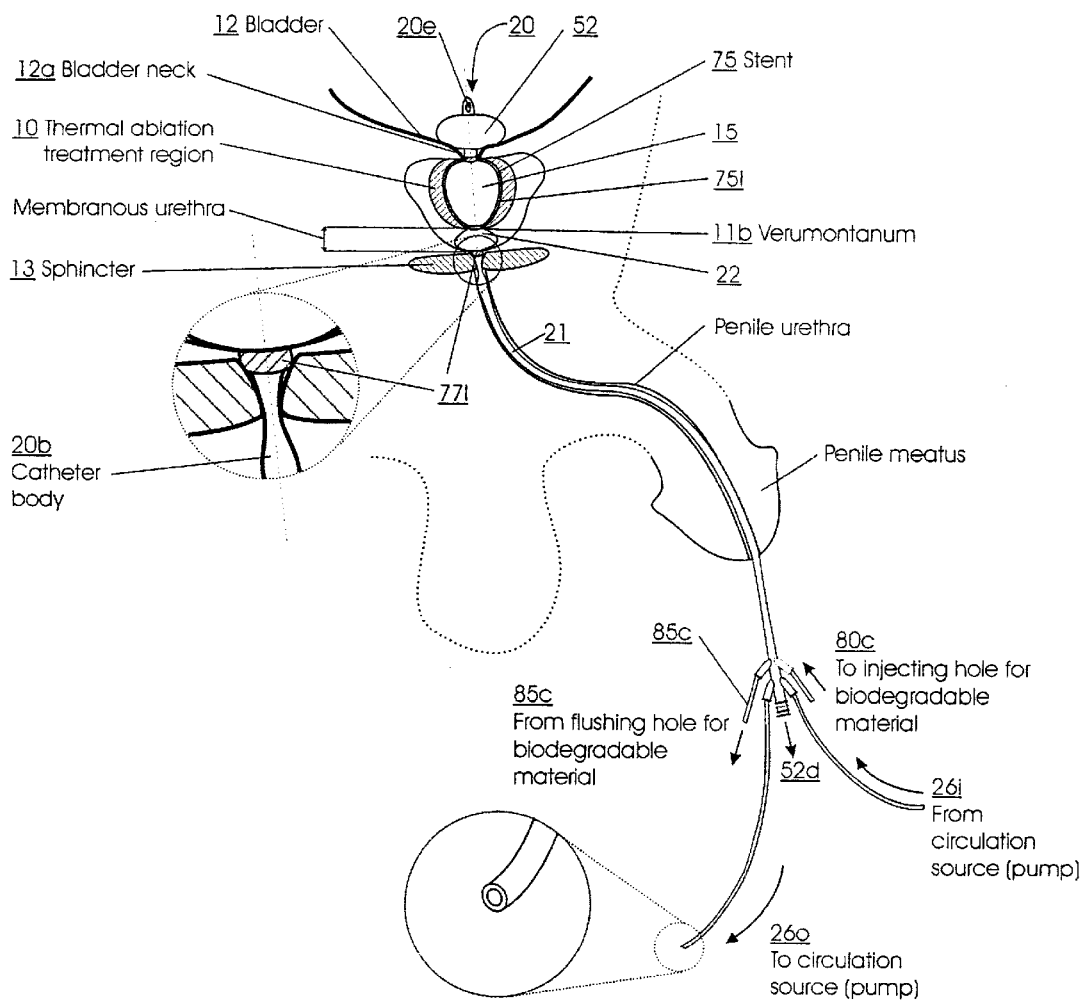
FIG. 1A is a schematic illustration of the anatomy of the male urethra showing a treatment catheter and a thermal ablation treatment region in the prostate according to embodiments of the present invention.

Referring now to the figures, the treatment catheter 20 shown in FIG. 1A, may be configured to supply the ablation therapy with any desired suitable heating source including RF, microwave, laser, ultrasound, circulating heated fluid, resistive heating, and the like. The heat can be directed at the tissue proximate the (expanded) treatment balloon. Employing circulating heated fluid may be particularly suitable for administering the thermal ablation procedure and also to activate and form the biocompatible stent 75 in situ.

As shown in FIG. 1A, thermal ablation therapy be carried out in a localized treatment region within the prostatic urethra, the treatment region 10 being generally described as including the upper portion of the urethra (termed the prostatic urethra) so as to extend generally below the bladder neck and above the verumontanum 11b of the subject. Alternatively, the treatment region 10 may include the bladder neck or a portion of the bladder neck itself. A suitable thermal treatment system is available from ArgoMed, Inc. located in Cary, N.C. See also, U.S. Pat. Nos. 5,257,977 and 5,549,559 to Eshel, and co-assigned U.S. patent application Ser. No. 09/433,952 to Eshel et al, the contents of which are hereby incorporated by reference as if recited in full herein.

Referring again to FIG. 1A, the thermal ablation treatment region 10 is indicated by the shaded lined region in the prostate above the sphincter 13. In operation, an elongated flexible treatment catheter 20 with an outwardly expandable treatment balloon 15 is inserted into the penile meatus along the penile urethra and positioned in the prostatic urethra and secured so that the treatment balloon 15 resides at the desired targeted tissue. In this embodiment, the treatment catheter 20 includes an axially extending shaft 21 and a urine discharge port 20e that is in fluid communication with a urine discharge or drainage channel 52d that allows urine to drain from the bladder through the catheter 20 while the catheter is in the subject. The treatment catheter 20 also includes a bladder anchoring balloon 52, the outwardly expandable treatment balloon 15, and, in certain embodiments, a lower blocking balloon 22. The treatment balloon 15 is configured to reside proximate the prostatic urethra above the membranous urethra. The lower blocking balloon 22, when used, is configured to reside above the urinary sphincter 13 in the membraneous urethra (and proximate the verumontanum). The treatment catheter 20 is also configured to supply and form in situ a biodegradable biocompatible stent 75 (shown as a stent layer 75l in FIG. 1A) that has selective fluent and non-fluent states to the treated region. Upon removal of the catheter 20 from the subject, the stent 75 remains in position in a non-fluent state (FIG. 1C) and in intimate contact with the prostatic urethra so as to inhibit closure of the prostatic urethra during edema or post-healing inflammation or swelling (as indicated by the lateral inwardly oriented arrows shown in FIG. 10E).

Figure 1B:
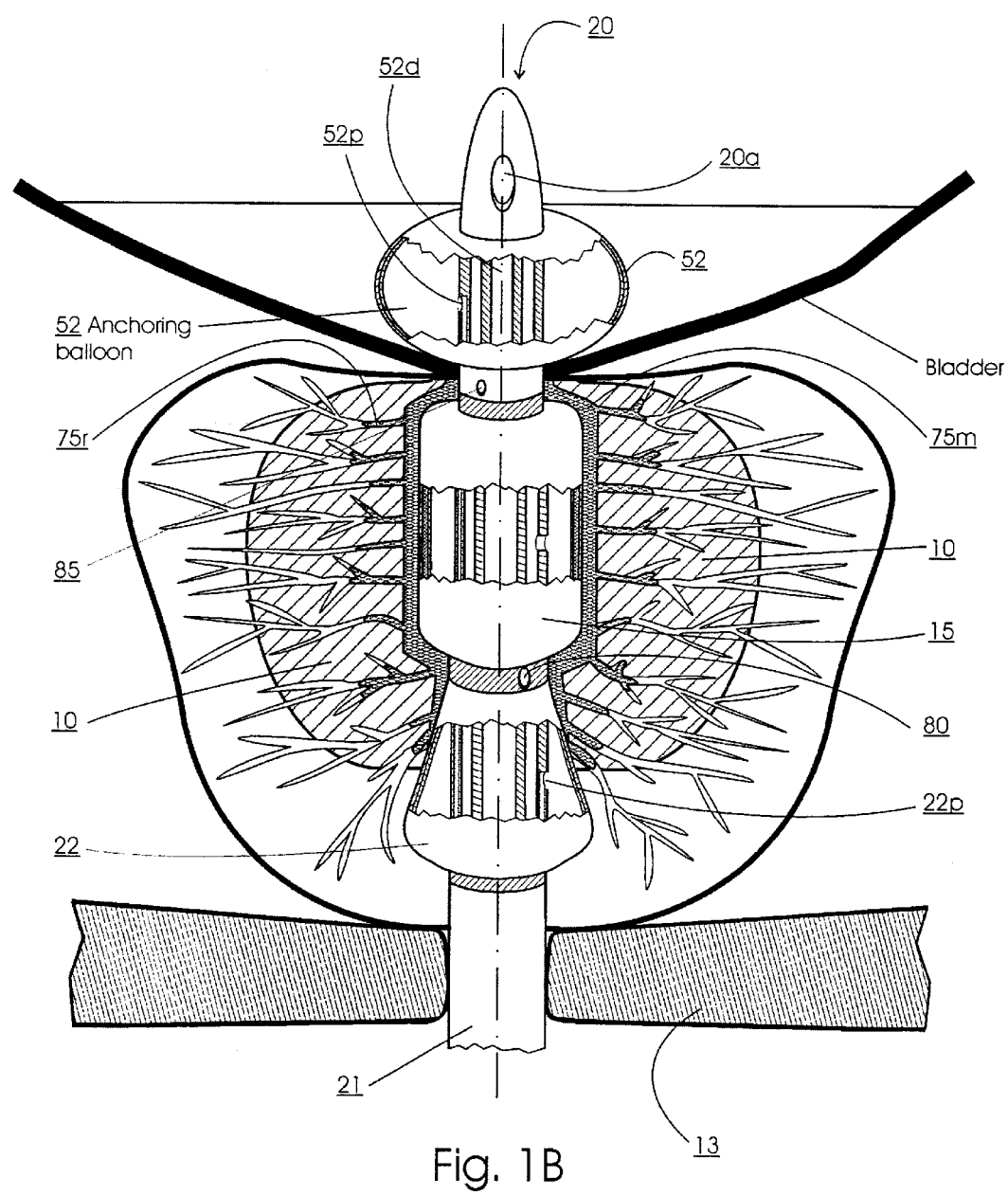
FIG. 1B is a greatly enlarged partial front view of a treatment catheter according to embodiments of the present invention illustrating the release of flowable biocompatible biodegradeable stent material while in position in the subject.
Figure 1C:
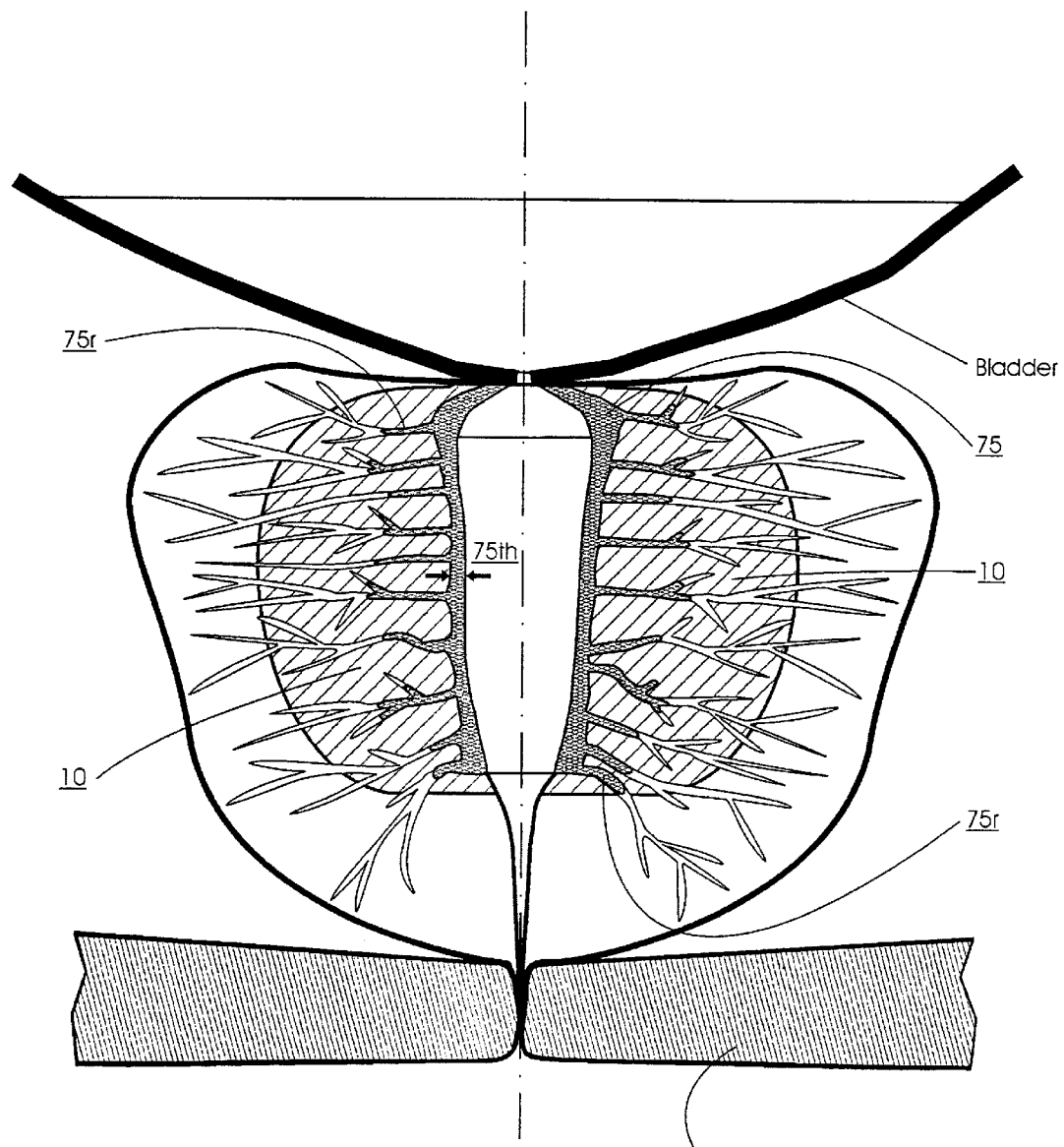
FIG. 1C is a schematic view of an ablated region of the prostate with a biocompatible biodegradeable stent according to embodiments of the present invention in position in the subject after removal of the treatment catheter so as to be in intimate contact with the ablated tissue.
Figure 2A:
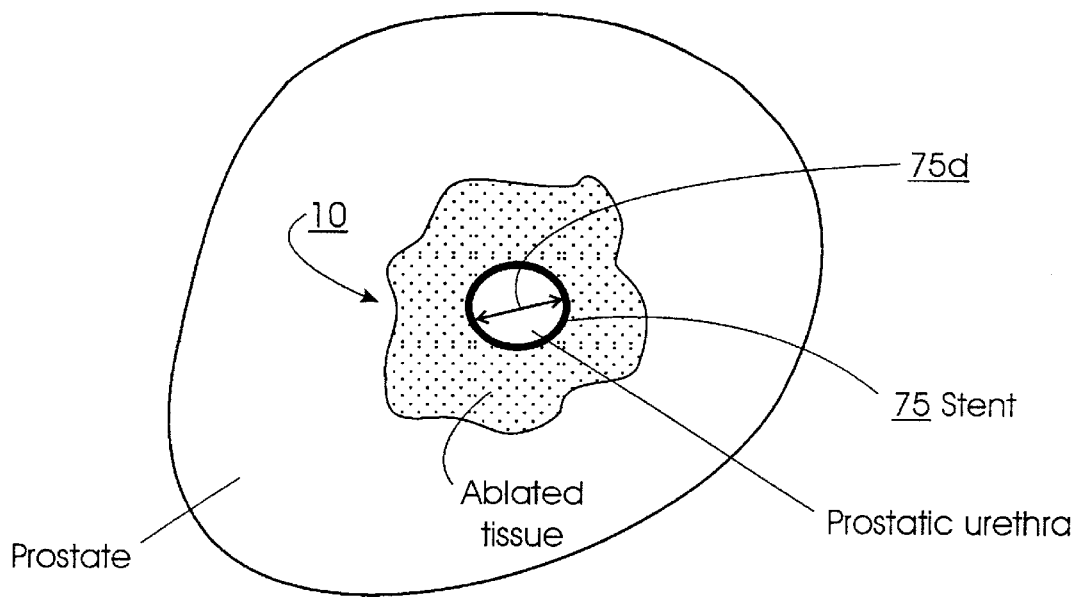
FIG. 2A is a sectional view of the prostate illustrating the ablated tissue with the biocompatible biodegradable stent according to embodiments of the present invention secured to the ablated tissue to inhibit closure of the prostatic urethra.
Figure 2B:
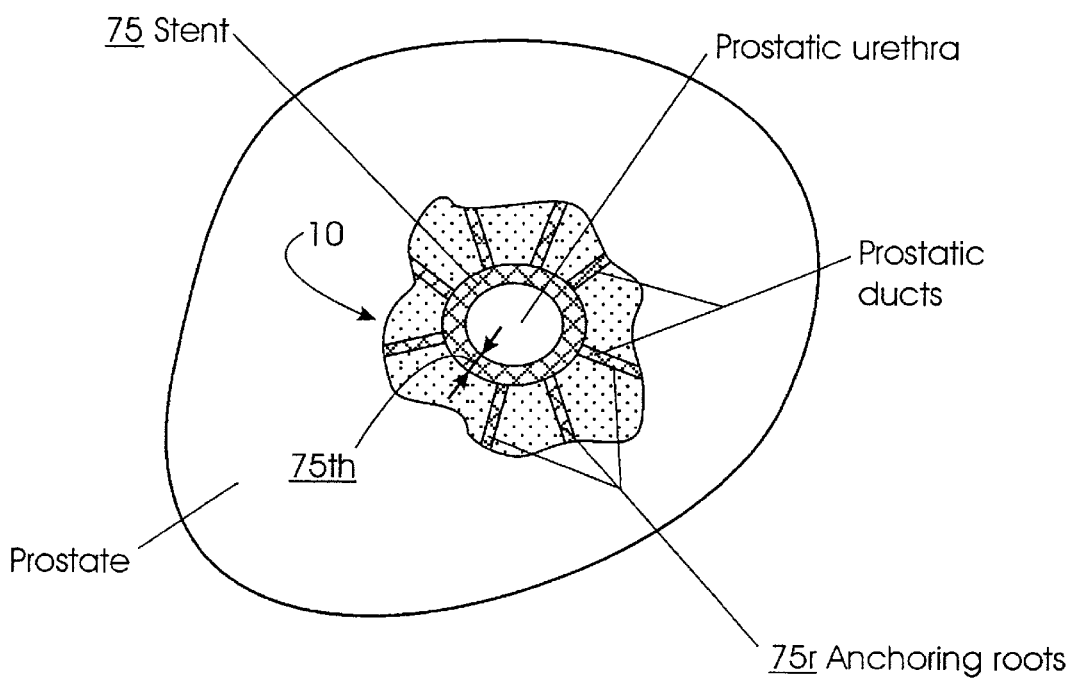
FIG. 2B is a sectional view of the prostate illustrating the ablated tissue with a biocompatible biodegradable stent according to embodiments of the present invention secured to the ablated tissue and in the acini ducts to thereby bolster the structural integrity of the stent.

As shown in FIGS. 1C, 2A, and 2B, in certain embodiments, the stent 75 is conformably formed and resiliently configured such that it can follow the contours of the urethra and provide a substantially smooth exposed inner surface while having sufficient rigidity to maintain a sufficiently sized opening in the prostatic urethra treatment region to allow urine drainage during the healing period. In particular embodiments, the stent 75 is configured so as to have good mechanical biocompatibility to sustain a desired opening size 75d (FIG. 2A) but sufficiently compliant so as to reduce the likelihood of introducing injury or shearing the proximate tissue.

As such, the stent 75 can be formed of a suitable material and thickness 75th as to be able to maintain a desirable opening size in the prostatic urethra lumen when exposed to compressive swelling pressures in the localized treatment region. Typically the stent body is able to maintain a sufficient opening size when exposed to compressive pressures from the treated tissue, these pressures may be on the order of about 7–21 psi. In certain embodiments, as illustrated in FIGS. 1C and 2B, the stent 75 has a thickness 75th of between about 1–3 mm (on average) along the length of the prostate proximate the location of the treatment balloon 15. The stent 75 may provide increased size for the prostatic urethra to discharge urine over the use of conventional Foley type catheters during the first 0–72 hours post-treatment. In certain embodiments, the stent 75 when formed against the urethra walls can be configured to define an inner diameter and corresponding opening width 75d of about 5–25 mm, and typically about 10–20 mm.

In the fluent state, the flowable stent material 75m (FIG. 1B) is typically a viscous or semi-viscous fluidic material that can be released from the catheter 20 to be able to disperse, travel or migrate away from the catheter to contact the walls of the prostatic urethra. The stent material 75m that forms the stent can be delivered to the prostatic tissue before, during, or after (but proximate in time to) the administration of the thermal ablation therapy. The treatment balloon 15 may be used to press, shape, or form the fluent stent material 75m against the wall. Once formed and/or in position in the body, the flowable stent material can be activated or transformed into the non-fluent state to conform to the inner surface of the prostatic urethra. In certain embodiments, the stent material 75m, stent layer 75l and/or stent 75 can be formed so as to be a good heat conductor. The term "good heat conductor" means that at ablation temperatures, the temperature drop across the stent or stent material is about 0.5 degrees or less.

Examples of suitable flowable biocompatible biodegradable stent materials that have fluent and non-fluent selectively transformable states are well known and include, but are not limited to, biodegradable biocompatible polymeric materials including polymers and copolymers and mixtures thereof. As used herein, the term "biodegradable" can include bioabsorbable and/or bioerodable or biodischargeable materials that are non-permanent and removed by natural or imposed physiological, biological, chemical or therapeutic processes. For more description of examples of suitable polymeric materials, see U.S. Pat. Nos. 4,702,917; 5,634,946; 5,575,815; 5,674,287; and 5,674, 192; the contents of which are hereby incorporated by reference as if recited in full herein. The polymeric materials may also include other additives such as plasticizers, medicaments and the like.

In certain embodiments, material compositions that include polycaprolactones may be particularly suitable as a bioabsorbable polymer that can be selectively formulated and/or configured for a relatively short degradation process in the body of between about 2 weeks to five or six months, and typically about 2 weeks to about 2 months, by selecting the proper composition, formulation, or formation method (such as by adjusting through copolymerization).

The polycaprolactone has a crystalline melting point of 60° C. It is noted that polyanhydrides have been described as suitable for drug matrix delivery and have relatively low glass transition temperatures (such as near body temperature).

The stent material 75m may comprise medicaments such as therapeutic or symptomatic treatment substances, pharmaceutical agents or drugs, bioactive substances, or food supplements, and the like, used to treat conditions of the prostate (such as BPH) or its symptoms that can be suspended as a matrix in the stent 75 and released in a time matrix format to facilitate the healing process and/or the treatment of the prostate. The medicaments can be ejected from the catheter before, during, or after the positioning of the fluent stent material 75m in the prostatic urethra either before, after, or during the transformation of the stent material to the non-fluent state. Examples of medicaments will be discussed further below.

In certain embodiments, such as in the configurations where the stent material 75m or stent 75 is positioned in the conductive heat path during the thermal ablation therapy, the material 75m can be formulated to be a good thermal conductor to allow for sufficient penetration of heat beyond the stent 75 and into the underlying prostatic tissue. As such, the stent material 75m can be selected so that it solidifies or becomes non-fluent at a desired time before, during, or after the thermal ablation treatment so as to not unduly interfere with the thermal ablation treatment, and then remains behind in the body after treatment and removal of the catheter 20.

The stent material 75m can be delivered to the target site in a fluent or non-fluent state and then subsequently released thereto before, during, or after the thermal ablation therapy in a number of different manners using a treatment catheter. For example, as shown in FIG. 1A, the stent material can be configured as a non-fluent outer shell or layer 75l disposed over the outer surface of the treatment balloon 15 on the catheter 20 so that, upon insertion, the stent layer 75l remains on the treatment balloon until a desired release time at which point it is transformed into a fluent state as will be discussed further below.

In certain embodiments, as shown in FIG. 1B, the stent material 75m can be introduced into the prostatic urethra so that it is able to travel a distance into the acini (prostate ducts or channels) in the prostate to form anchors or roots 75r (see also FIG. 1C) to help secure the stent 75 into the tissue in the body so that it has increased structural reinforcement capability). Introducing the stent material 75m with sufficient pressure and/or at a time during the thermal treatment can allow the stent material 75m to migrate into the channels to form roots or anchors 75r. In some embodiments, an internal massage therapy can be administered concurrently or serially with the thermal ablation therapy (such as by repetitively successively expanding and contracting the treatment balloon) at a time before or during the thermal ablation process. See co-pending and co-assigned U.S. Provisional Patent Application Serial No. 60/308,344, the contents of which are hereby incorporated by reference as if recited in full herein.

Figure 5A:
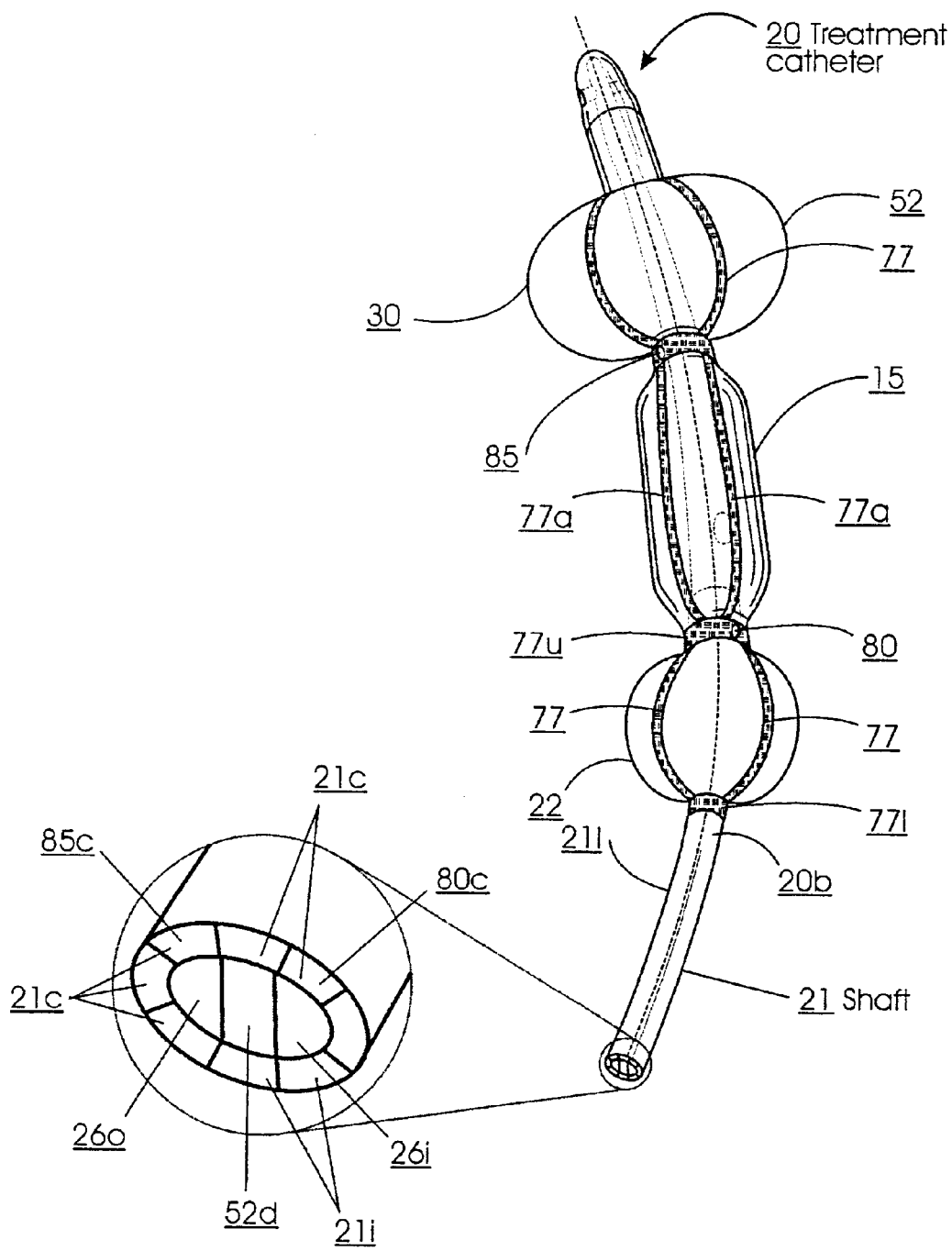
FIG. 5A is a perspective view of a treatment catheter according to embodiments of the present invention configured to deliver and apply the biocompatible biodegradable stent to the targeted region in the body.
Figure 5B:
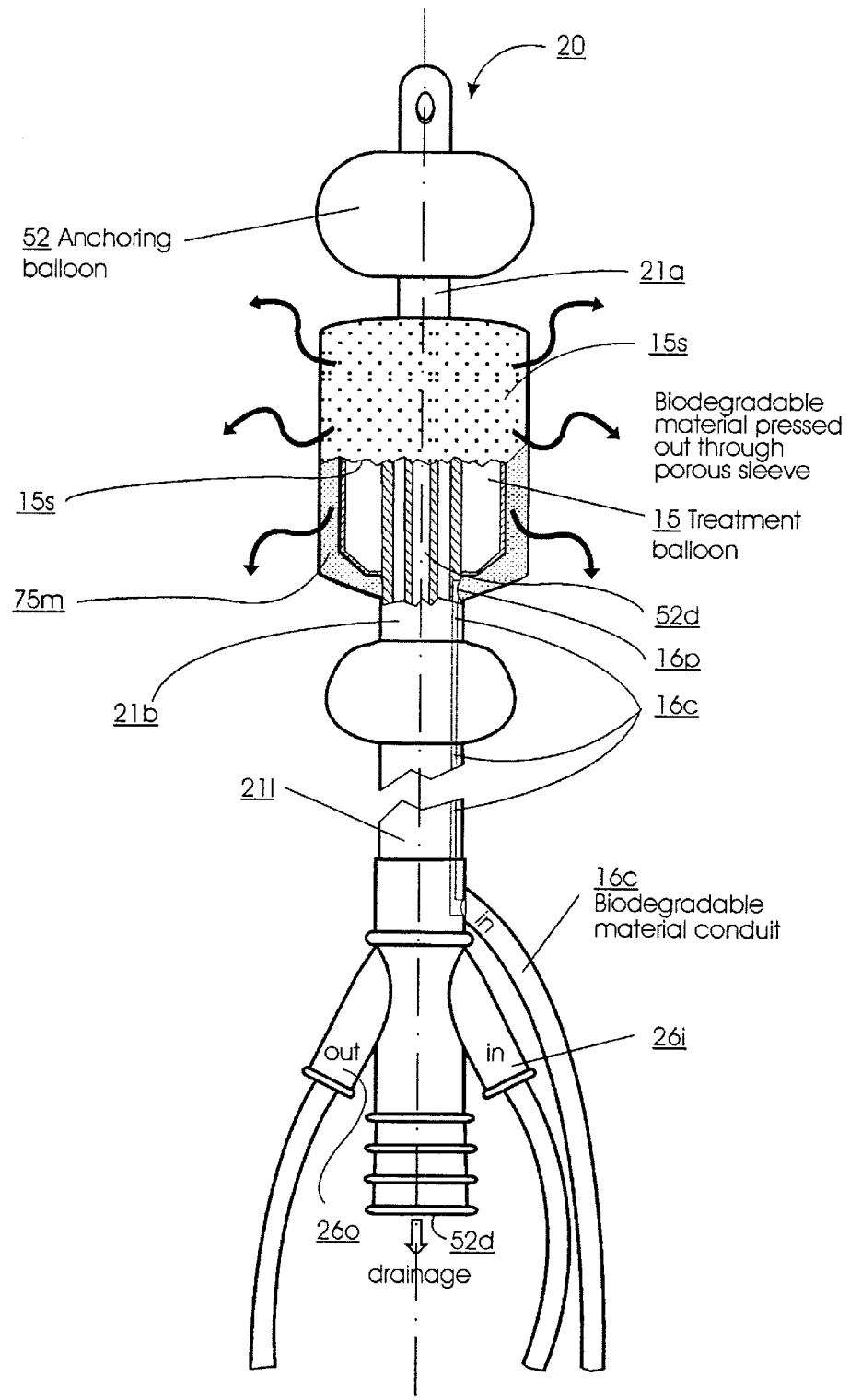
FIG. 5B is a front view of a treatment catheter according to other embodiments of the present invention.

In yet other embodiments, as shown in FIG. 5B, the fluent stent material 75m can be directed to exit a permeable or porous sleeve 15s that is positioned over the treatment balloon 15. The sleeve 15s can be configured to be concurrently expandable with the treatment balloon as well as independently expandable responsive to the quantity of fluent stent material 75m that is directed to flow from the sleeve inlet port 16p and associated flow channel 16c. The sleeve 15 may be configured as a low thermal resistance elastic sleeve that helps the catheter maintain a low profile upon insertion and removal to force the treatment balloon tightly against the surface of the shaft, even after exposure to ablation level temperatures. The sleeve 15s is elastic and can be formed from an elastomeric material having a Shore A (Type A) durometer range of between about 20 and about 60. The thickness of the elastic sleeve 15s can, in certain embodiments, be between about 0.005 inches and about 0.030 inches (about 0.127–0.762 mm). Typically, the sleeve 15s should be configured so as to not substantially interfere with the heat transfer from the underlying treatment balloon 15 during the thermal ablation treatment. Elastomeric materials that may be suitable to form the sleeve 15s include, but are not limited to, silicone, natural rubber, synthetic rubber, and plasticized polyvinylchloride (PVC). In certain embodiments, the permeable or porous sleeve 15s may be used in combination with the dispersing and/or flushing ports and channels as desired.

In particular embodiments, the sleeve 15s may also be formed of biodegradable materials. For the biodegradable materials, the sleeve 15s (or a portion thereof) may be configured such that it is absorbed into the body over time or so that it dissolves after it enters the body at some point in time before, during, or after the treatment. As such, in certain particular embodiments, the sleeve 15s may be used to form the stent 75. Examples of suitable biodegradable materials include polymers, copolymers and polymer compositions. Exemplary biocompatible biodegradable absorbable materials were described above and others are described in U.S. Pat. Nos. 6,171,338; 4,743,257; 4,700,704; 4,655,497; 4,649,921; 4,559,945; 4,532,928; 4,605,730; 4,441,496; 4,435,590; and 4,559,945. The contents of these patents are hereby incorporated by reference as if recited in full herein. Additional description of suitable sleeves can be found in co-pending and co-assigned U.S. Provisional Application Serial No. 60/288,774, the contents of which are hereby incorporated by reference as if recited in full herein.

In other embodiments, as shown in FIG. 1B, fluent stent material 75m is flowably directed up in the catheter via one or more flow channels so that it travels through the catheter 20 to be released from one or more injection or dispersing apertures 80 formed in the outer wall of the catheter 20 about the treatment region. The at least one dispersing aperture 80 may be positioned in the shaft 21 above and/or below the treatment balloon 15 and includes an associated material flow channel 80c (FIGS. 5A, 6B). A plurality of spatially separated dispersing apertures 80 may be used, each in fluid communication with a common or individual flow channel. In certain embodiments, at least one (or a plurality of radially spaced) dispersing apertures 80 can be positioned both above and below the treatment balloon 15 so that a sufficient quantity of fluent stent material 75m can be distributed and/or sprayed about the prostatic urethra as shown in FIG. 10C.

Figure 3:
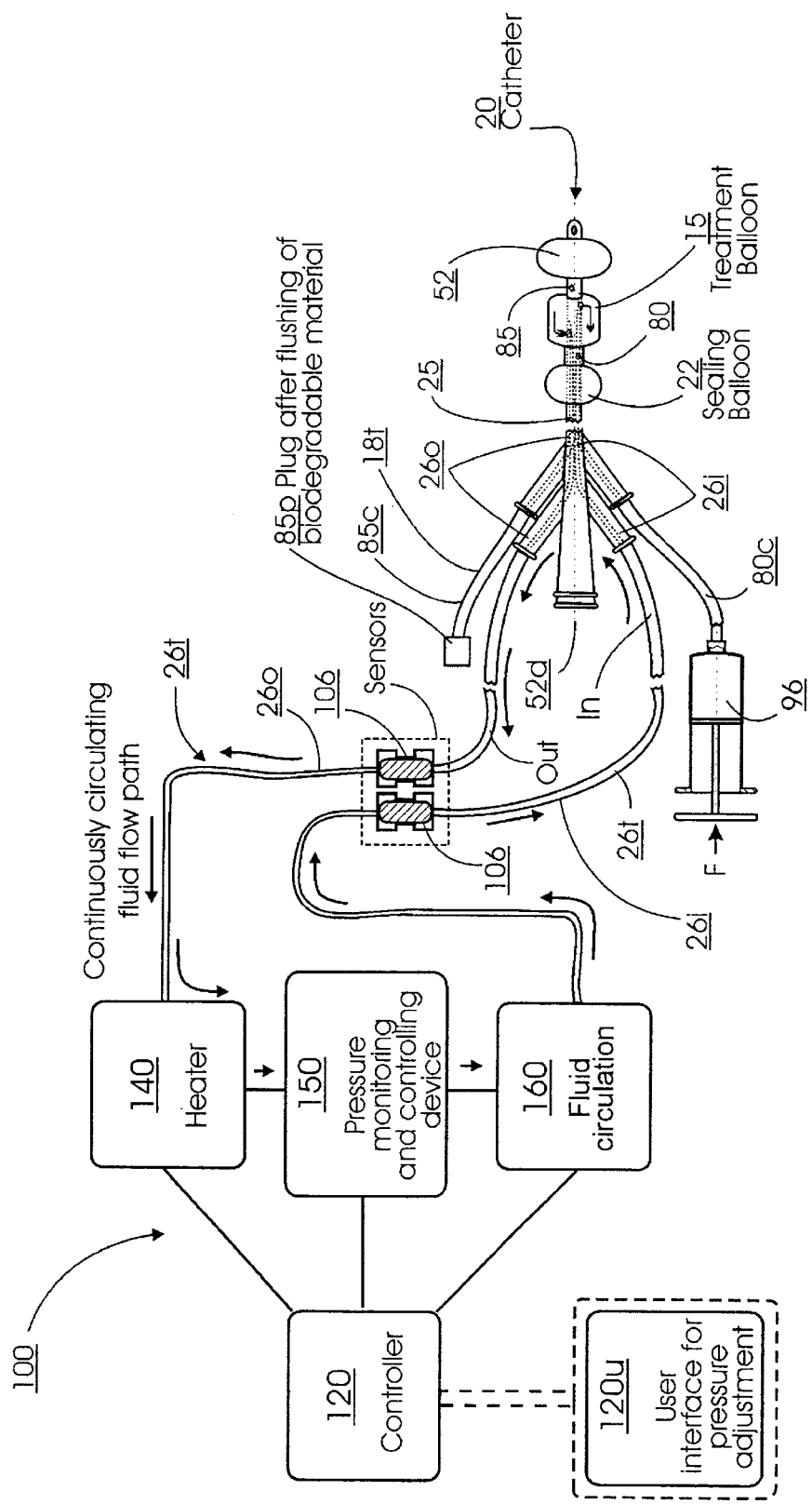
FIG. 3 is a schematic illustration of a closed loop circulating fluid system according to embodiments of the present invention that is configured to both thermally ablate the targeted tissue and deliver and conform the biocompatible biodegradable stent material to the walls of the prostatic urethra.

In certain embodiments, as shown in FIG. 1B, one or more dispersing or injection apertures 80 may be positioned below the treatment balloon 15 and one or more flushing apertures 85, each having a common, shared, or separate associated flushing channel, can be located above the treatment balloon 15. The treatment balloon 15 may be partially or wholly deflated when the stent material 75m is ejected from the dispersing ports 80. The stent material 75m can be forcibly ejected from the dispersing ports 80 under pressure such that the stent material 75m rises to the location proximate the flushing port 85. The upper flushing port 85 may be sized and configured to be smaller than the dispersing port 80 so as to impede or reduce the amount of stent material 75m that flows therein (thereby keeping a substantial or major portion of the material 75m in the prostatic urethra). In particular embodiments, the flushing port 85 may be from about 10–75% smaller in width than the dispersing port 80. In operation, a quantity of stent material 75m will then enter the flushing port 85 and travel through the associated flushing channel 85c (FIGS. 5A, 6C) to exit the catheter 20. A clinician can monitor the external orifice of the flushing channel 85c to determine when/if sufficient quantity of fluent stent material 75m has been distributed and/or circulated or delivered in vivo based on the confirmation that a suitable quantity has exited the catheter via the flushing channel(s) 85c (that is in fluid isolation from the flow channel (s) 80c). The external orifice of the channel (such as via flexible tubing 18t) associated with the flushing port 85 can be closed or blocked off (with a valve means or plug) 85p after sufficient quantity has exited the catheter to terminate excess leakage of stent material 75m from the body as shown in FIG. 3.

Although not required, in certain embodiments as shown in FIGS. 1B, 5A, and 6A, the treatment catheter 20 may also include a lower sealing balloon 22. Prior to releasing the stent material 75m in fluent form from the catheter, the sealing balloon 22 can be expanded to contact the walls of the membraneous urethra to substantially seal the urethra above the sphincter. In this manner, the stent material 75m is inhibited from flowing below the sealing balloon 22. The sealing balloon 22 can be concurrently inflatable with the treatment balloon 15 (in fluid communication therewith) or separately inflatable having its own inflation channel, inflation port and source.

As shown in FIG. 1A, the sealing balloon 22 can be configured to take on a shape that can be described as a pear shape, ramped or inclined shape, or frusto-conical shape, when expanded. This allows the profile of the sealing balloon 22 to taper out from the top to the bottom, thereby inhibiting movement of the catheter 20 toward the sphincter 13 when the sphincter 13 relaxes or opens. In addition, this shape may also inhibit upward movement of the catheter body toward the bladder, as the upper portion of the prostatic urethra, especially when the treated tissue is swollen, inflamed or suffering from edema, tends to close down or restrict the opening area in this region. Thus, the sealing balloon 22, which can be positioned in the in the membranous urethra, will abut the restricted opening size of the urethral canal thereabove, in the treatment region, thereby inhibiting upward movement or migration of the catheter 20. Of course, the present invention is not limited thereto and other balloon shapes may also be employed, as may corresponding elastic sleeves with various shapes and configurations including, but not limited to, pear shapes, ramped or inclined shapes, bulbous shapes, elliptical shapes, oval shapes, cylindrical shapes, accordion pleated shapes, shapes with tapered fins (such as circumferentially disposed about the perimeter of the lower portion of the stent body), and the like. Similarly, the anchoring balloon 52 may be configured in any suitable shape.

In operation, and independent of the delivery mechanism or configuration, the fluent material 75m can be pressed against the wall or interior surface of the prostatic urethra by the expansion of the treatment balloon 15 and then transformed into a non-fluent state by exposing the stent material 75m to an activation mechanism or reaction source such as chemical (polymerization or cross-linking), electrical, or mechanical, including, but not limited to, heating, cooling, or exposing the fluent material 75m to light in situ.

In other embodiments, two different fluent materials or material mixtures (one containing the initiator) can be directed to travel through the catheter in fluid isolation and ejected from the catheter separately under pressure so that they mix in situ to react to transform the combined mixture into the biocompatible biodegradable non-fluent stent. One of the materials or material mixtures may be directed to exit the catheter through the porous or permeable sleeve 15s, or each may have its own ejection channel and port.

As shown in FIG. 5A, the lower portion of the shaft 21l of the catheter can include elongated channels 21c that can function as fluid flow channels (such as channels 80c and/or 85c that are in fluid communication with injecting/dispersing aperture 80 and flushing aperture 85, respectively) and/or can provide increased shaft insulation 21i that encases one or more internal fluid lumens 21c (such as the drainage channel 52d, and/or inlet and outlet circulating fluid channels 26*i*, 26*o* or other desired flow paths) as desired for particular embodiments of the invention. As shown, the increased insulation 21*i* can include a number of axially extending channels that encase the inner lumens. See co-assigned concurrently filed U.S. application Ser. No. 10/011,700, entitled Treatment Catheters with Thermally Insulated Regions, for additional description of catheter insulation configurations, the contents of which are hereby incorporated by reference as if recited in full herein.

FIG. 6A illustrates another embodiment of a catheter 20 that can be configured to be conformable to the contours of the urethra upon insertion and includes a plurality of elongated channels 21*c* that define increased insulation 21*i* for a lower portion of the shaft 21. FIGS. 6B and 6D illustrate different elongated outer and inner channel configurations (and/or wall structures). As shown, one of these channels 21*c* is the fluid material flow channel 80*c*. Other of the channels 21*c* can be used to inflate the anchoring balloon 52 and the sealing balloon 22 (and may also be used to supply the sleeve with fluid material or to direct medicaments to the treatment region where desired). The elongated channels 21*c* encase internal fluid lumens such as the drainage channel 52*d* and the inlet and outlet fluid circulating channels 26*i*, 26*o*, respectively. FIG. 6C illustrates a different view taken about the flushing port. As shown, one of the elongated channels 21*c*, is in fluid communication with the flushing port 85 and provides the associated flushing channel 85*c*.

Figure 8:
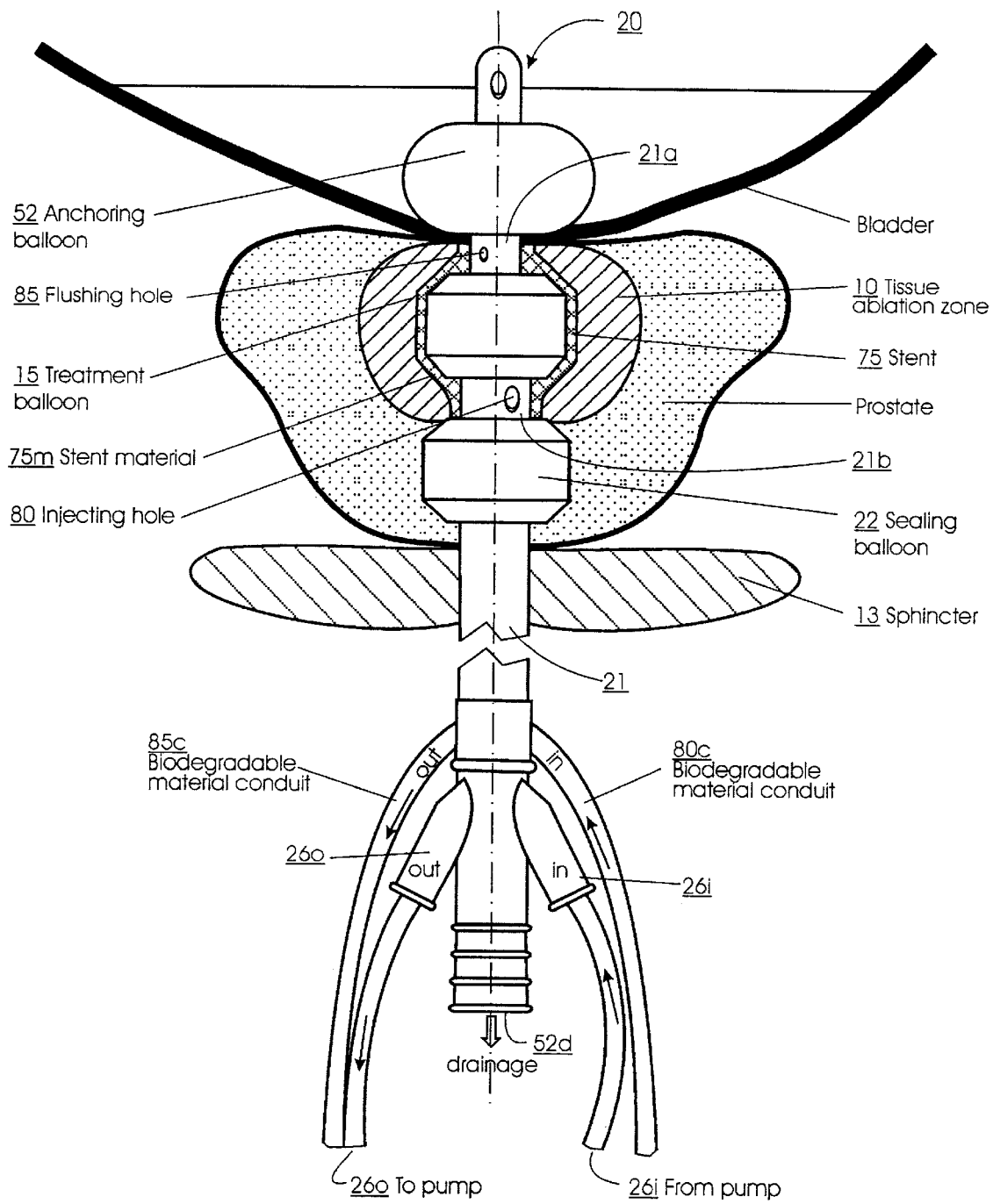
FIG. 8 is a front view of a treatment catheter according to embodiments of the present invention in position in the body and contacting and pressing the biocompatible biodegradeable stent material proximate thereto.

FIG. 8 illustrates the treatment catheter 20 in position in the subject with the stent material 75*m* released therefrom and positioned about the prostatic urethra. As shown, the stent material 75*m* extends an axial length that corresponds to the distance between the lower portion of the anchoring balloon 52 and the upper portion of the sealing balloon 22.

Figure 7:
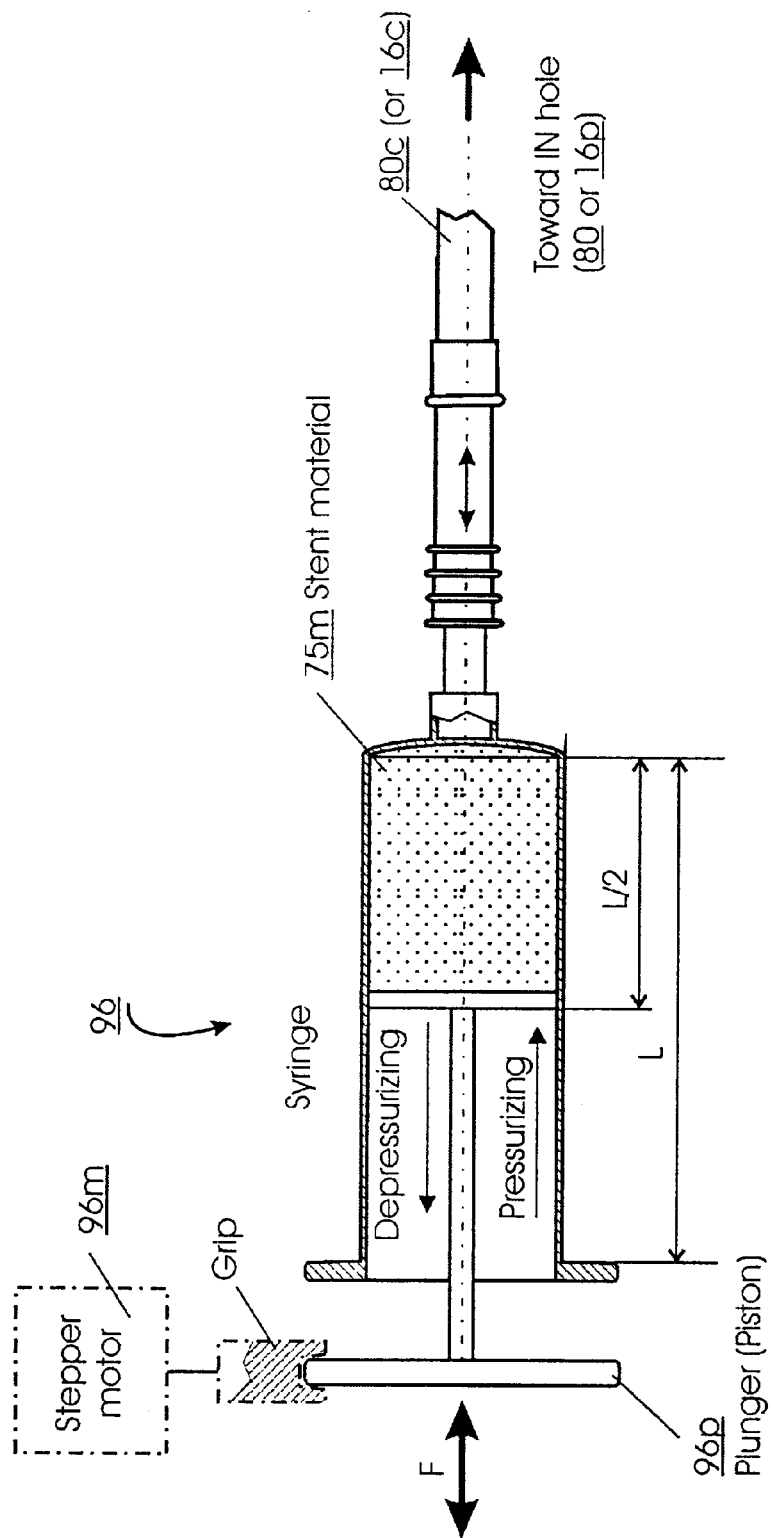
FIG. 7 is a partial side section view of a treatment catheter and flowable stent material injection device according to embodiments of the present invention.

FIG. 7 illustrates that a syringe 96 with a quantity of stent material 75*m* that may be used to engage with the desired flow channel(s) in the catheter to deliver the stent material to the dispersing port(s) 80 (and/or to flow channel 16*c* then to sleeve port 16*p*) under pressure. An exemplary quantity of stent material 75*m* that may be deployed to form the suitable stent thickness and size, includes, but is not limited to, at least about 20 ml–100 ml. The syringe 96 may be manually operated or automatically operated such as via a stepper motor 96*m* that automatically translates the plunger 96*p* of the syringe 96 to inject the stent material under pressure. A pressure sensor (not shown) may be employed to allow a controlled pressure release as desired.

Figure 9A:
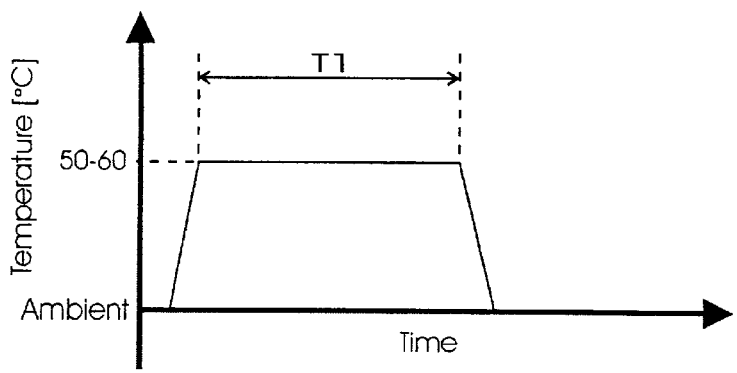
FIGS. 9A–9D are graphs of the operative temperatures over time for treatment sessions according to embodiments of the present invention using treatment systems to deliver thermal ablation treatments as well as biocompatible biodegradable stents according to embodiments of the activation temperatures.

FIGS. 9A–9D illustrate examples of temperature cycles over a treatment session that can be used to administer a thermal ablation therapy and to transform the stent material 75*m* to its desired fluent and/or non-fluent forms during, before, or after the thermal ablation therapy. FIG. 9A illustrates that the stent material can be released or placed into the prostate before the thermal therapy and the thermal ablation therapy can be administered at a substantially constant temperature of between about 50–60° C. (for a time "T1"). As such, the ablation energy travels through the stent 75 such that it either becomes non-fluent early in the ablation treatment session or becomes non-fluent when the temperature is ramped down to body temperature at the end of the treatment session.

Figure 9B:
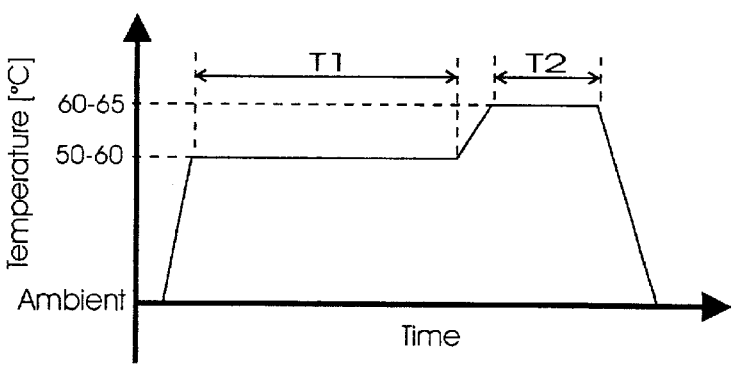

FIG. 9B illustrates that the treatment can be carried out a first ablation temperature threshold for a major portion of the therapeutic treatment ("T1") and then elevated to a second increased temperature toward the end of the treatment session ("T2"). In this embodiment, the stent material 75*m* may be located in the body prior to the initiation of the treatment (such as an outer layer on the treatment balloon 15) but the stent 75 does not become non-fluent until after the time designated as "T1" when it reaches its activation threshold.

Figure 9C:
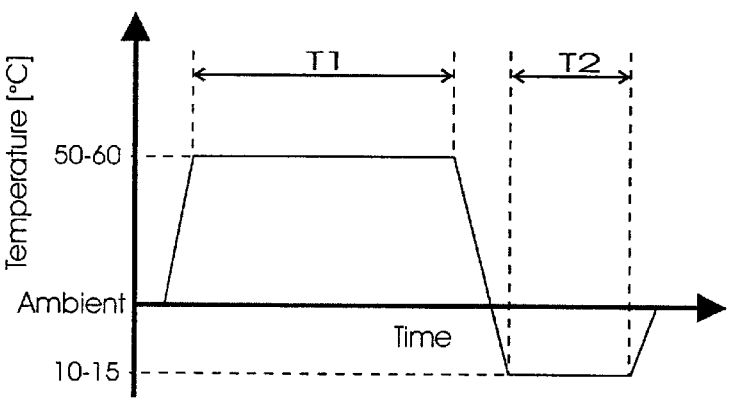

FIG. 9C illustrates that the ablation therapy can be carried out and then the stent material 75*m* cooled at time T2 to cause it to become non-fluent. The stent material can be introduced between times T1 and T2 or during or before T1.

Figure 9D:
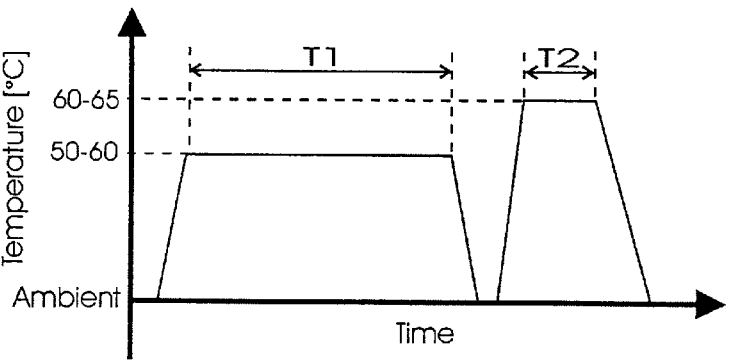

FIG. 9D illustrates that the thermal ablation therapy can be carried out at a first threshold level similar to FIG. 9B, and after the thermal therapy is completed, the thermal source is interrupted to insert the flowable material into the prostatic urethra. Then an activation thermal cycle can be commenced during time and a second selected temperature "T2" to transform the stent material 75*m* to its non-fluent form. Alternatively, a major portion of the thermal treatment can be administered (that may be represented by the time "T1") and then interrupted for a brief period to insert the material 75*m* and then completed at a different temperature level during time T2.

Other treatment temperature cycles and timing may also be used according to the ablation temperatures desired, depth of penetration desired, and stent material and composition and configuration employed as will be appreciated by those of skill in the art.

In certain embodiments, to allow for ease of retraction of the catheter after applying the thermal therapy and forming the stent 75, as shown in FIGS. 5B, 6A, 8 and 10A–10E, a portion of the shaft 21*b*, that portion that extends below the treatment balloon 15, can be configured to have a diameter or width that is greater than the portion of the catheter shaft 21*a* that is above the treatment balloon (the portion intermediate the treatment balloon 15 and the anchoring balloon 52). The larger shaft 21*b* can be sized so as to accommodate the dimension of the anchoring balloon 52 and treatment balloon 15 over its shaft (when deflated). As such, the increased size portion of the shaft 21*b* may be about 5–25% larger than the (upper) reduced size portion 21*a*.

As shown in FIG. 5A, certain portions of the catheter 20 such as the bottom portion of the catheter 20*b* that resides above the sphincter 13 can be configured to have radio-opaque indicia 77 (as denoted by the shaded region along the upper portion of the catheter. The indicia 77 can be any suitable radio-opaque feature such as a marker, surface, layer, or other feature so as to be imageable or visualized in an X-ray (to allow external positional verification of the device). FIG. 5A illustrates that a series of radio-opaque markers may be employed, some axially extending and some radially extending to help confirm the positional location of the catheter when in the subject, irrespective of its orientation in the body. The stent material may also be configured to be externally detectable (such as with a radio-opaque dye or other additive/composition) so as to allow external positional verification by X-ray or other desired means. As such, X-rays can be taken at insertion/placement (initial positioning) and can also be taken periodically during to confirm proper positioning in the subject in situ.

As shown in FIG. 5A, the radio-opaque markers 77 can be circumferentially arranged on the catheter either or both above 77*u* and below 77*l* (see also FIG. 1A) the sealing balloon 22 so that the balloon 22 can be more readily accentuated and confirmed in the X-ray as located in the membranous urethra, above the sphincter. Alternatively, or additionally, as shown in FIG. 5A, one or more longitudinally extending radiopaque markers 77a can be arranged to extend substantially along the length of the treatment balloon 15 at various radial positions (preferably at least 4 positions symmetrically separated and aligned about the cross-sectional width of the catheter, typically at 90 degree radial separation to allow for X-ray identification irrespective of the image angle). The radio-opaque markers are applied to block the transmission of X-ray for better contrast in images. The opacity, degree of contrast, and sharpness of the image may vary with material and type of process used to create the marker. The radio-opaque marker(s) may be arranged on the catheter by any suitable biocompatible marker, such as non-toxic radiopaque coatings, inks, thin-films, paints, tapes, strips, shrink tubing, and the like. See e.g., Richard Sahagian, *Critical Insight: Marking Devices with Radiopaque Coatings,* Medical Device & Diagnostic Industry (May, 1999), also available at URL deviceline.com/mddi/archive/99/05/011.html. Other examples of radiopaque markers include polyolefin inks available as No-Tox® Medical Device Polyolefin Inks from Colorcon, and resin compounds with barium sulfate and/or bismuth such as is available from New England Urethane Inc. of North Haven, Conn. See also Danilychev et al., *Improving Adhesion Characteristics of Wire Insulation Surfaces,* Wire Technology International, March 1994 (discussing various treatments such as gas plasma treatment systems for medical products) which may be appropriate for use in the fabrication of the catheter 20.

As an alternative to (or in addition to) forming the medicaments into the stent 75, medication, drugs, treatments, rinses, and the like can be introduced into the subject through an external medication port inlet and associated channel. The channel can be the urinary drainage channel 52d or other of the elongated channels 21c in the catheter or can be formed as its own separate channel and release port (not shown). The fluid (or mixture) can be directed to exit a desired port after the fluid travels through the catheter to the treatment site or proximate the treatment site. The medication inlet port can be provided with any suitable valve/port device as is known to those of skill in the art. Suitable valve devices (for both the inflation system and the medication delivery system) are available from medical device manufacturers such as Alaris Medical Systems (SmartSite® system) and B. Braun. The medication can be used to reduce edema, inhibit bacterial infections, reduce the likelihood of UTI or treat the onset of UTI or otherwise promote healing and/or treatment.

Figure 11:
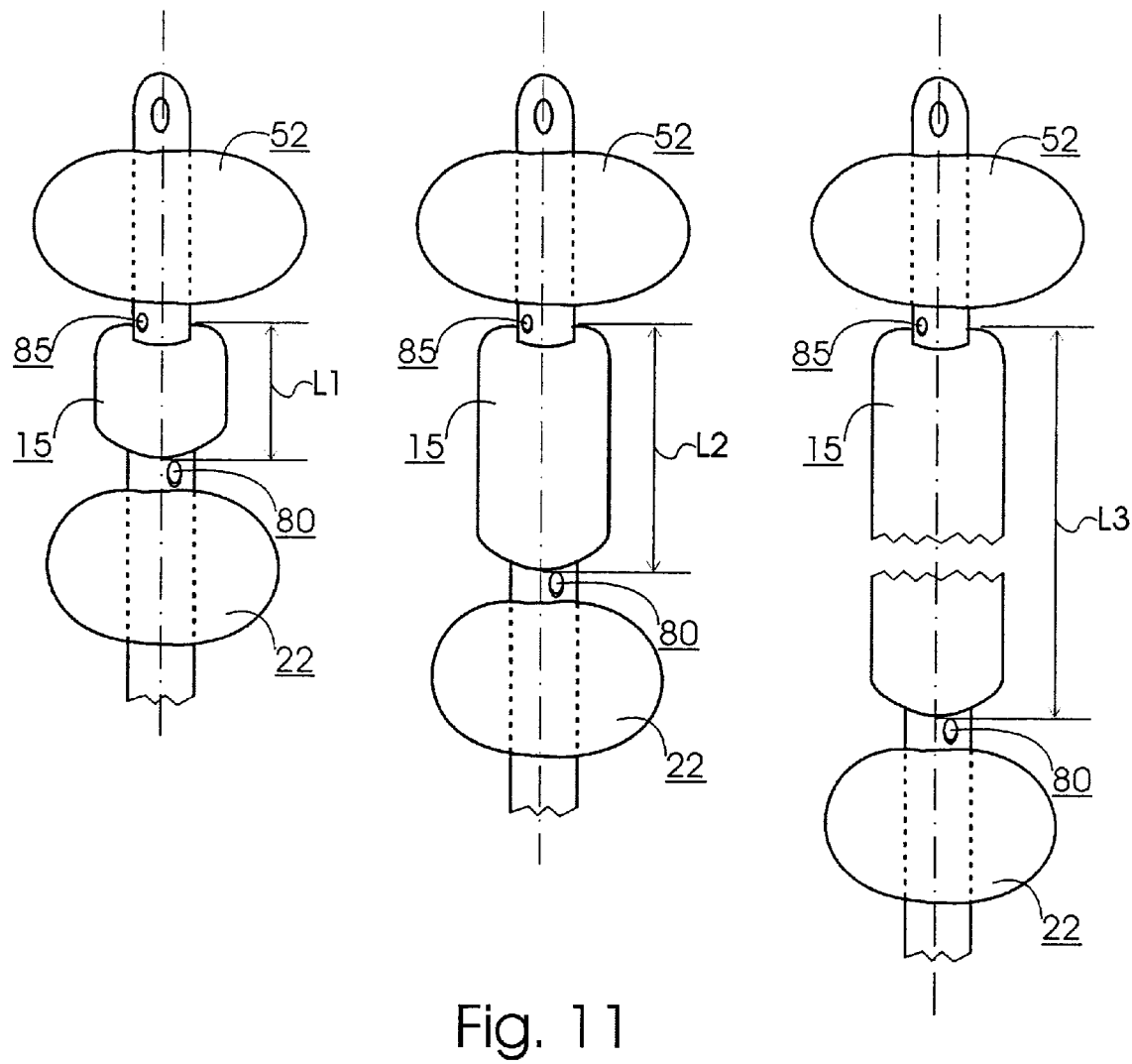
FIG. 11 is a front partial view of a set of treatment catheters according to embodiments of the present invention.

As shown in FIG. 11, the treatment balloon 15 may be provided in several lengths from about 3–12 cm, and typically from about 1–6 cm. The catheters 20 may be provided as a set with a range of lengths (such as in 0.5 cm increments) so as to allow a clinician to select from an easy compliment of assorted sizes and thus readily employ the size that fits the patient. Thus, the catheters may be provided as a kit or set of catheters as shown in FIG. 11 with various lengths of treatment balloons 15 with the ports 80, 85 positioned at opposing ends of the treatment balloon (above and below) thereon.

The outer surface of the catheter 20 can be configured with a biocompatible lubricant or low-friction material to help reduce discomfort associated with the insertion of the catheter device into the body as well as to promote the separation of the treatment balloon from the stent material 75m in the body. Coatings that may be appropriate include coatings that promote lubricity, and wettability. For example, a hydrophilic coating which is applied as a thin (on the order of about 0.5–50 microns thick) layer which is chemically bonded with UV light over the external surface of the stent 20. One such product is a hydrophilic polymer identified as Hydrolene® available from SurModics, Inc., of Eden Prairie, Minn. Other similar products are also available from the same source. Still further, the catheter 20 can be configured not only to provide the lubricious coating but to also include bioactive ingredients configured to provide sustained release of antibiotics, antimicrobial, and anti-restenosis agents, identified as LubrilLast™ from AST as noted above. One suitable material may be the antimicrobial silver zeolite based product available from HealthShield Technologies LLC of Wakefield, Mass. Another alternative is a Photolink® Infection Resistance antimicrobial coating or a hemocompatible coating from SurModics, Inc. of Eden Prairie, Minn. The coating may also include other bioactive ingredients (with or without the antimicrobial coating), such as antibiotics, and the like. One product is identified as LubriLAST™ lubricious coatings from AST of Billerica, Mass.

The flow channel 80c, dispersing port 80, and/or flushing channel and port 85c, 85 can also be used to collect fluid specimens from the prostate region during the treatment (via gravity feed or suction and the like). Typically, the specimen is obtained prior to releasing the stent material into the prostatic urethra cavity. These types of internal prostatic fluid specimens may be collected in a manner that is representative of its condition in the body (substantially void of urine and the like) to allow for a better specimen for analysis. See co-pending and co-assigned U.S. Provisional Patent Application Serial No. 60/330,029.

In addition, although the closed end configurations of the catheter 20 shown herein have been illustrated as substantially upright, they can also be curved into other configurations such as Coude or Tiemen.

Medicaments that may be incorporated into the stent 75 (such as in a slow release matrix formulation) and/or delivered separately include, but are not limited to, analgesics, anti-depressants, phytotherapy therapeutics such as PEE-NUTS or PROSTA-Q, anti-inflammatory agents such as steroid inhibitors (such as COX-2 inhibitors like VIOXX) and PENTOSAN POLYSULFATE, non-steroid inhibitors, antibiotics, neuroleptic agents (such as ELVAIL, NEURONTIN, DOXEPIN, and MARCAINE), α-blockers (such as PHENOXIBENZAMINE), specific immunology modulators such as ENBREL (by Immunex, a drug approved by the FDA for rheumatoid arthritis), bioflavinoids to reduce the level or oxidants in the prostatic fluid, FINASTERIDE, TERAZOSIN, ALFUZOSIN, antioxidants, quercitan, and the like, and combinations thereof.

FIG. 3 illustrates one embodiment of a thermal treatment system 100 that can be configured as a closed loop circulating fluid system. In particular embodiments, the closed loop system 100 can be configured as a low-volume system to circulate between about 20–100 ml at any one time through the system (including the catheter 20 and the tubing 26t). The system 100 includes a fluid circulation pump 160, a pressure monitoring and controlling device 150, a heater 140, temperature sensors 106, and a controller 120. The system 100 can be configured with a patient interface device 120u to allow a patient to adjust the treatment pressure. The arrows in the figure illustrate the direction of the circulating fluid flow in the system and catheter.

In certain embodiments, as discussed above, the stent material flow channel 80c can also be used to obtain a prostatic fluid specimen from the prostate. Thus, the syringe 96 may be replaced with a pump or length of conduit that connects to the existing circulation pump 160 to draw or direct the fluid therein to discharge downstream of the pump 160 into a biosample collection chamber or container to provide the suction force to obtain the prostatic fluid biosample. In other embodiments, gravity, capillary action, or other collecting means may be employed. See e.g., U.S. patent application Ser. No. 09/433,952 and U.S. Pat. No. 5,549,559, the contents of which are hereby incorporated by reference as if recited in full herein, for descriptions of a suitable closed loop circulating fluid system. Fluid circulating WIT catheters with expandable treatment balloons are available from ArgoMed, Inc., in Cary, N.C. The pressure in the treatment balloon (which corresponds to the pressure in the closed loop system) may be from about 0.5–4 atm, and typically at least about 0.75–2 atm during at least a portion of the treatment to increase the force (that may be pulsatile) presented to the localized tissue.

In certain embodiments, the circulation can be provided by using a peristaltic pump to generate pulsatile fluid flow. A three-roller pump may be configured to operate to provide about 1–12 or 1–20 expansion and contraction pulses per second to about 1–12 or 1–20 pulses per minute in the balloon. In particular embodiments, this action can be caused by using a pulsatile flow pump having three rollers with between about 200–750 rotations per minute while a two roller pump may be configured to operate with between about 200–500 rotations per minute; each can operate so as to provide a corresponding number of pulses to the treatment balloon. Suitable pump heads are available from Watson Marlow Inc., of Wilmington, Mass., and Bamant Co., of Barrington, Ill. Of course, other methods for expanding and contracting a treatment balloon or generating the pulsatile flow can also be used as will be appreciated by those of skill in the art.

Turning now to FIG. 4, operations for a method for treating the prostate and inhibiting the obstruction of the prostatic urethra after thermal ablation (or resection or other inflammatory procedure) according to the present invention, is shown. First, a treatment catheter is position in the subject so that a treatment balloon resides proximate the prostatic tissue (block 200) and administers a thermal ablation treatment (block 205). Flowable stent material that is selectively transformable from fluent to non-fluent states is released from the thermal ablation treatment catheter in a fluent state to reside about the prostatic urethra (block 210). The flowable stent material can be a viscous or semi-viscous material in the fluent state. The fluent stent material can be formed or pressed against the prostatic urethra wall or inner surface by expanding the treatment balloon (block 220). The stent material is activated in situ to cure or become non-fluent and form the stent in the body (block 230). The stent material can be activated via heat (block 222), cooling (block 223), exposure to light (ultraviolet, etc) (block 224), or by chemical reaction (block 225). The treatment catheter is removed from the subject leaving the stent in the treatment region (block 240).

The flowable stent material can be introduced before, after, or during the administration of the thermal ablation therapy and then activated in situ to form a resilient biodegradable biocompatible stent that inhibits obstruction of the urethra during post-treatment healing (block 212). In certain embodiments, the flowable stent material can be configured to be applied via a non-fluent coating or layer applied to the outer surface of the treatment balloon that becomes fluent in the body when heated and then transforms back to its non-fluent state upon cooling to remain (block 214*a*). The stent material can be held in the catheter in a fluent state and dispersed from the treatment catheter in a fluent state (block 214*b*).

For particular embodiments of treating BPH, the catheter can be configured to circulate heated liquid in a closed loop system through the prostate. The circulating heated liquid is directed through the catheter to a treatment balloon such that it travels, captured in the catheter, through the penile meatus, along the penile urethra the bulbous urethra, and the membranous urethra to a localized treatment region in the prostate inside the treatment balloon. The tissue in the localized treatment region in the prostate is exposed to a temperature above about 45° C. for a predetermined thermal ablation treatment period by exposure to contact with the expanded balloon that contains the heated circulating liquid (typically at about 50–62° C. for more than about 20–60 minutes). As noted above, the localized treatment region can be an upper portion of the urethra (typically called the prostatic urethra), leaving the lower part of the urethra (the membranous urethra), non-ablated. As such, the liquid does not directly contact the tissue. This can be accomplished in closed loop circulating systems, which heat the liquid remotely, by insulating the shaft of the treatment catheter up to the treatment balloon to inhibit the exposure of non-targeted tissue to ablation temperatures.

In other embodiments, the circulating fluid can be heated to lower treatment temperatures, such as between 45–50° C., or even less than 45° C. (such as 35° C.–44° C.) to provide cooling at the localized tissue region and/or the stent material, as desired.

It will be understood that one or more blocks of the block diagrams and combinations of blocks in block diagram figures can be implemented or directed to be carried out by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus or associated hardware equipment to function in a particular manner diagrams. The operations or the blocks in the diagrams may be combined, separated, or carried out in a different order from that shown.

Figure 10A:
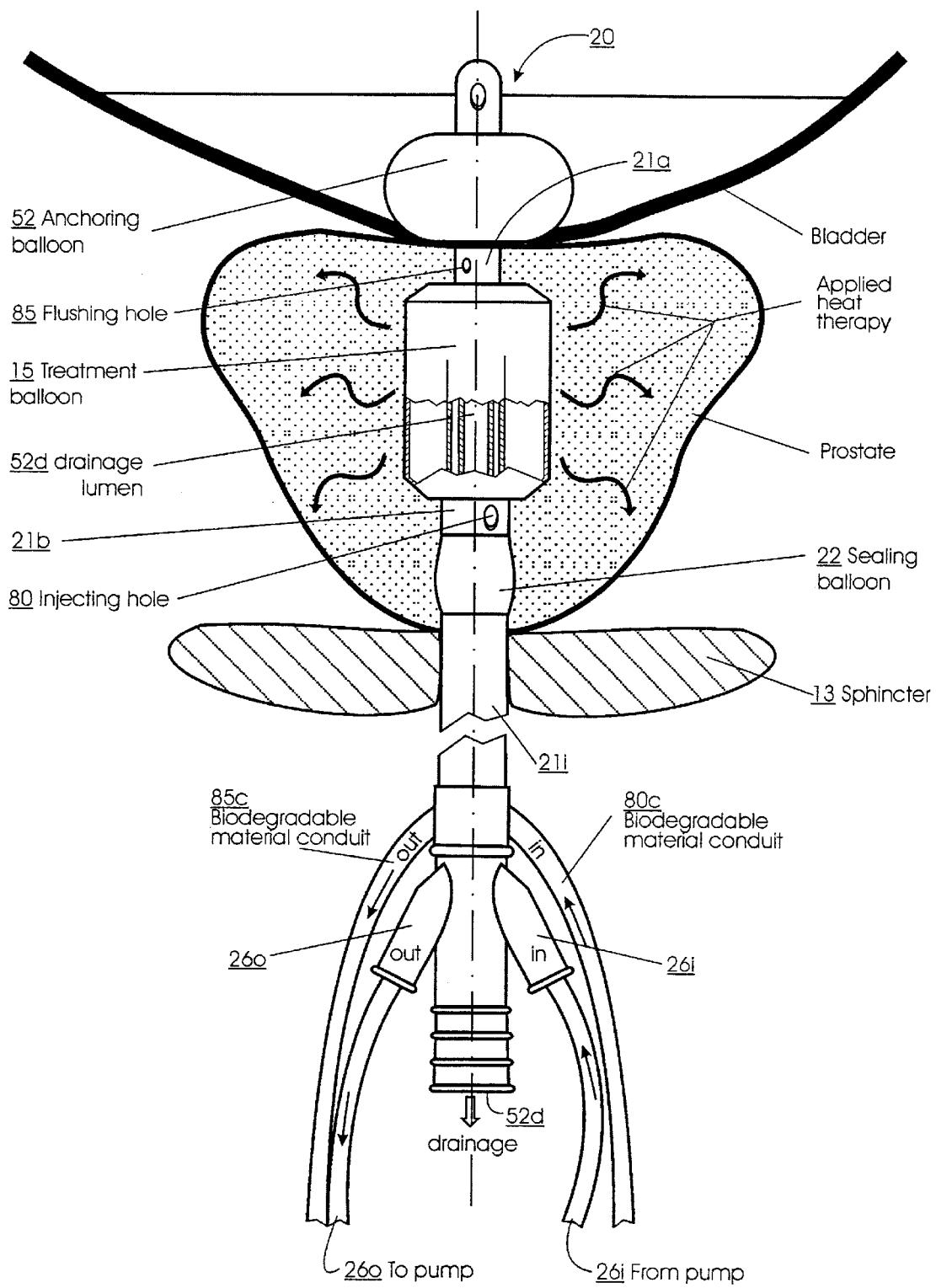
FIGS. 10A–10E illustrate operative configurations of an exemplary treatment catheter according to embodiments of the present invention during use in the subject.
Figure 10B:
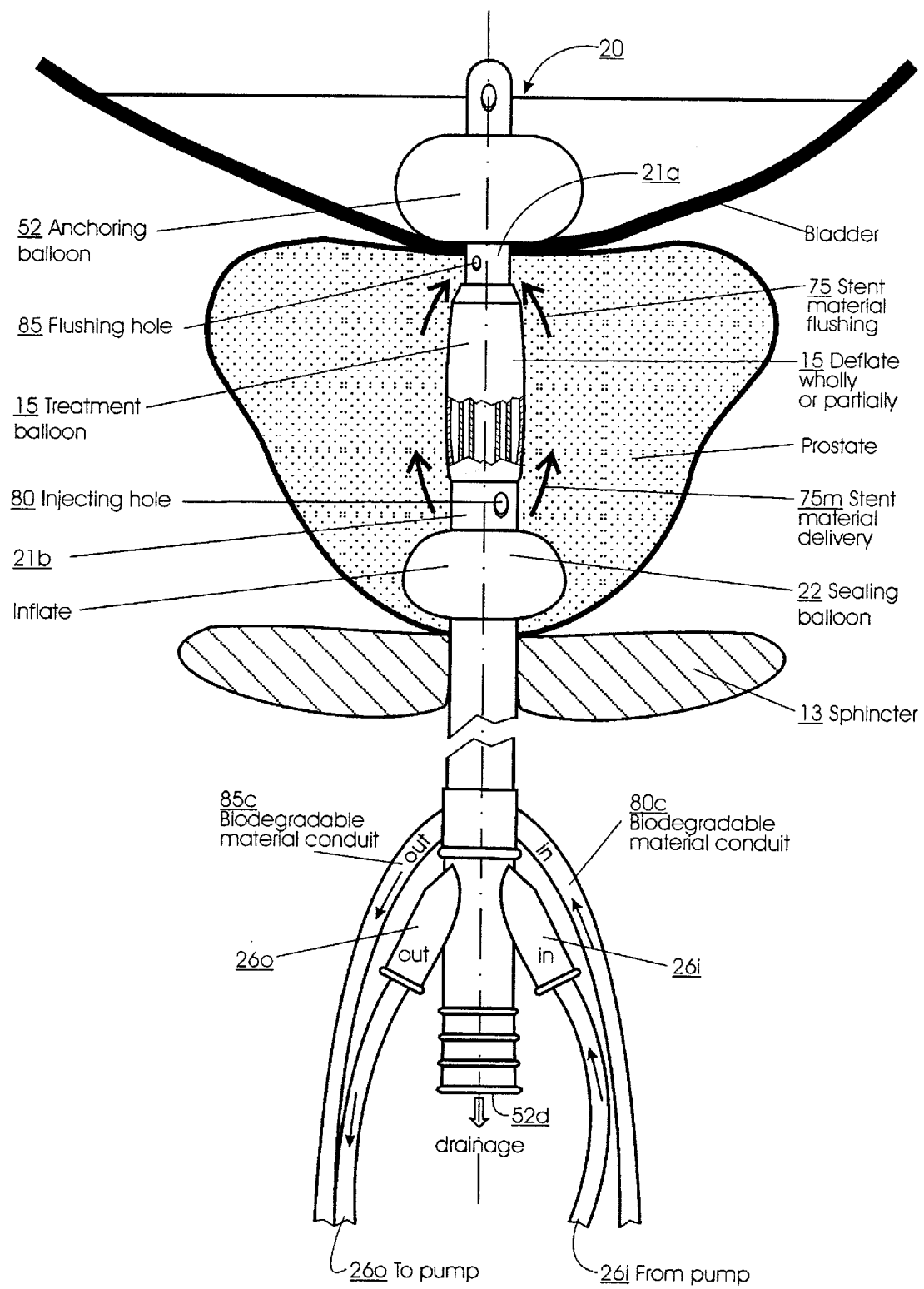
Figure 10C:
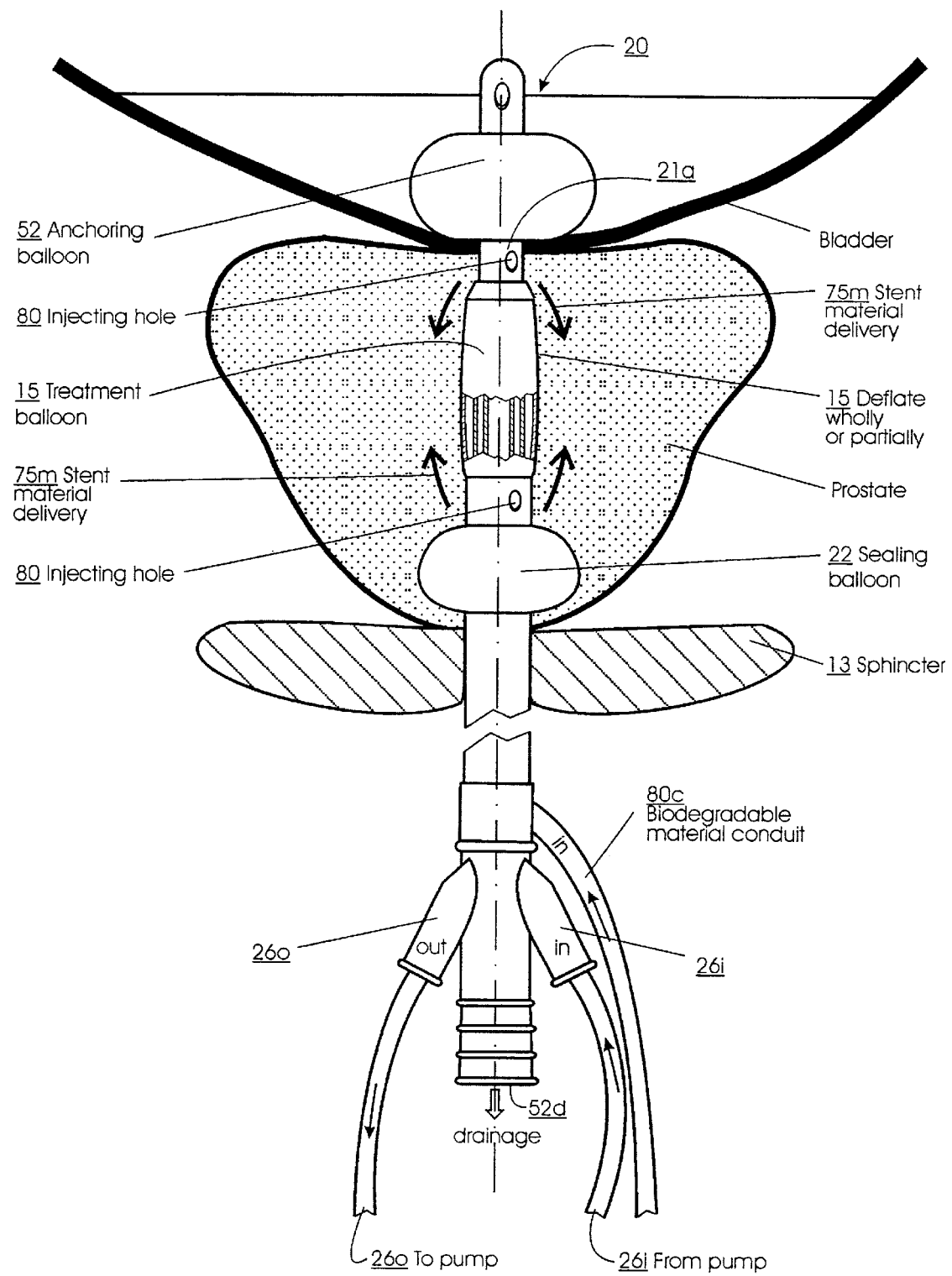

FIGS. 10A–10E illustrate operative configurations of an exemplary treatment catheter 20 according to embodiments of the present invention. FIG. 10A illustrates the treatment catheter 20 in position and administering a thermal therapy (such as a thermal ablation therapy) to the subject (the heat dispersion is shown by the lines with arrows in the prostate in the figure). During the thermal ablation therapy, the sealing balloon 22 can be deflated. FIG. 10B illustrates the release of fluent stent material 75*m* from the catheter and its movement upward away from the dispersing port(s) 80 to the flushing port(s) 85. The sealing balloon 22 is inflated to contact and substantially seal against the membraneous urethra to contain the material above the sphincter 13. As shown, the treatment balloon 15 may be partially or wholly deflated during this operation to allow the stent material to flow upwardly with less restriction. In particular embodiments, the stent material 75*m* can be introduced in sufficient quantity to substantially fill the prostatic cavity between the balloons 52 and 22 and the treatment balloon 15.

FIG. 10C illustrates an alternative configuration, whereby stent material 75*m* (shown by the dark lines with arrows) is released from dispersing ports located both above and below the treatment balloon 15 (that may be partially or wholly deflated).

Figure 10D:
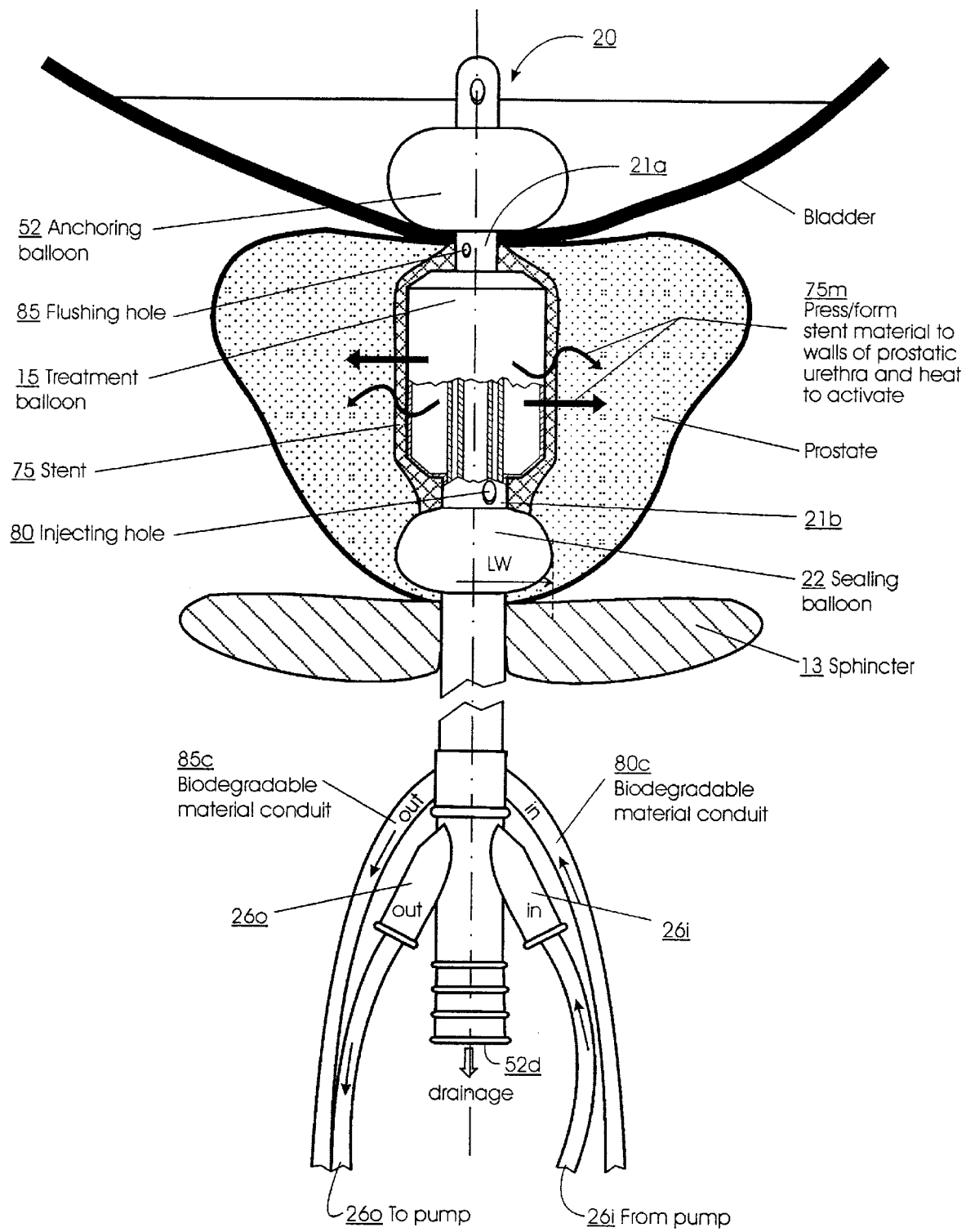
Figure 10E:
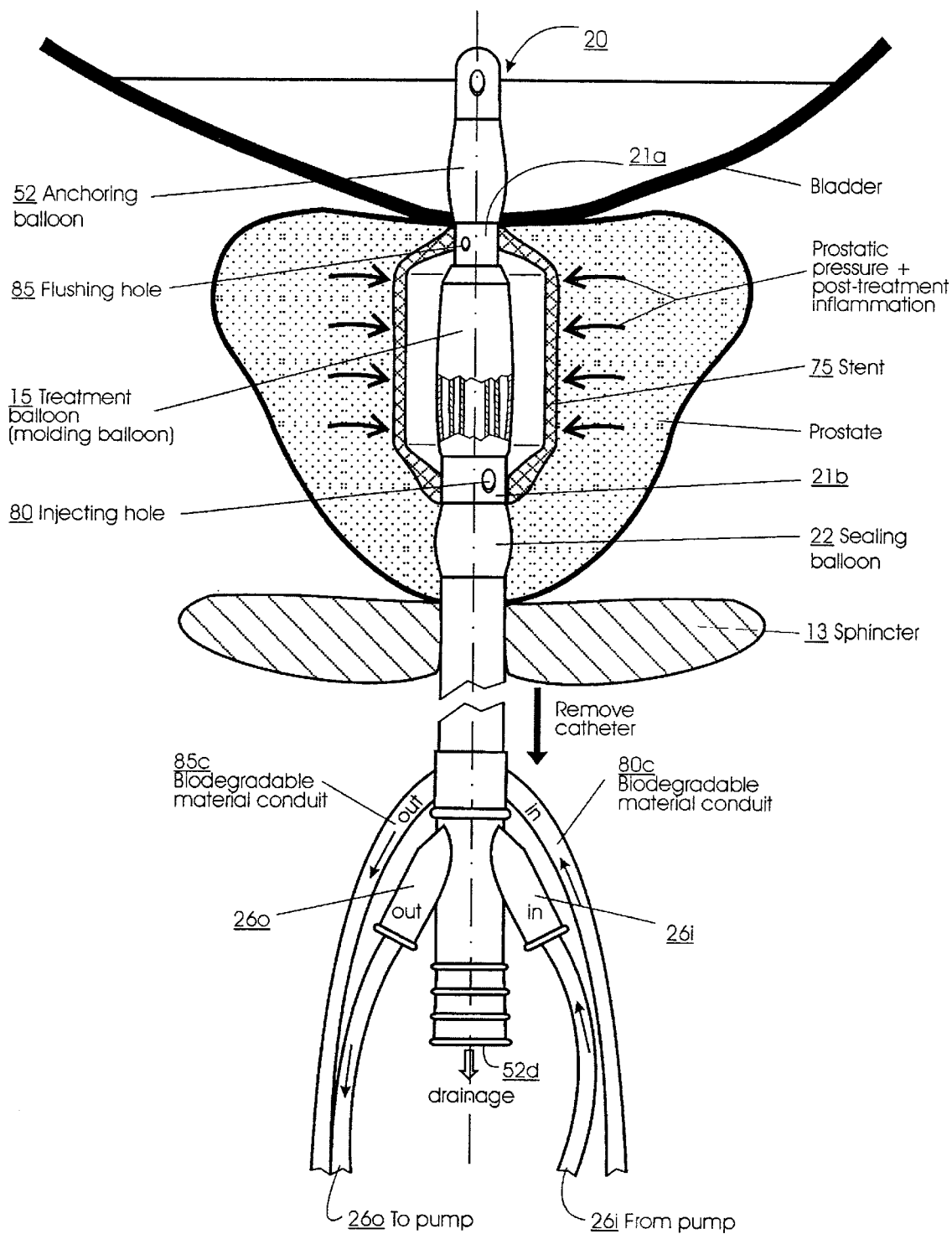

As is also shown in FIG. 10D, the sealing balloon 22 can be configured to expand a greater distance than the treatment balloon 15 (indicated by the width, "LW"). In any event, FIG. 10D shows that the treatment balloon 15 can be expanded to press and/or form the fluent stent material 75m to the walls of the prostatic urethra and to apply heat to activate or transform the stent material so as to make it non-fluent. FIG. 10E illustrates that to remove the catheter 20, all balloons 52, 25, 22, are deflated, and the stent 75 remains in position and inhibits the closure of the prostatic urethra during post-treatment inflammation (shown by the converging arrows directed at the urethra passage). It is noted that configuring the portion of the shaft 21b in the membraneous urethra below the treatment balloon with an increased width and/or diameter that reduces the interference of the stent 75 with the smaller sized upper portion of the shaft 21a and can inhibit the disruption and/or dislocation of the stent upon removal of the catheter.

FIG. 10D may also be referenced to illustrate another embodiment where the stent material 75m can be released from the treatment balloon 15 to radially disperse about the length of the treatment balloon 15. The stent material 75m can be released through a porous or permeable sleeve 15s. Alternatively, the stent material 75m can be configured as a nonfluent outer layer 75l formed over the treatment balloon 15 (FIG. 1A) as discussed above. FIG. 10D also illustrates the treatment balloon 15 can be expanded during this release as desired.

The biocompatible biodegradeable stents of the present invention can fuse with the urethral tissue. This bio-attachment can decrease the potential that the stent will dislocate from its intended location during the healing period and may be particularly suitable for treating conditions of the prostate having increased internal pressures such as inflammation of the prostate (such as is associated with postablation procedures and the like) and/or hyperplasia.

The methods and catheters of the present invention may be used for other applications, such as to treat and/or form biodegradable stents and the like for other natural lumens or body cavities that have periodic fluid or solid movement of biomaterials therethrough, such as the rectum, the colon, the cervix and/or uterus, the bladder, the throat, the ear, the nose, passages of the heart and/or associated valves, portions of the respiratory system, the esophagus, the stomach, bile ducts, and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A catheter for treating a condition of the prostate, comprising:

an elongated axially extending shaft;

a treatment balloon secured to the shaft and configured to expand outwardly therefrom;

an outwardly expandable permeable or porous sleeve configured to overlie the treatment balloon, the sleeve being independently inflatable from the treatment balloon;

a quantity of flowable biocompatible biodegradable stent material disposed intermediate the treatment balloon and the sleeve;

a bladder-anchoring balloon secured to the shaft above the treatment balloon and configured to expand outwardly from the shaft;

a sealing balloon secured to the shaft below the treatment balloon and configured to expand outwardly from the shaft;

a urinary drainage channel extending through the shaft; and a flowable fluent biocompatible stent material channel having at least one ejection port formed in the shaft in fluid communication with the sleeve so as to direct the flowable biocompatible stent material therein, the flowable material channel being in fluid isolation with the drainage channel;

wherein, in operation, the treatment balloon is adapted to inflate to press the flowable stent material released from the sleeve into the targeted tissue in the body.

2. A catheter according to claim 1, wherein the shaft is configured and sized such that the portion intermediate the treatment balloon and anchoring balloon has a decreased cross-sectional width relative to the portion of the shaft intermediate the treatment balloon and sealing balloon.

* * * * *